US009137996B2

(12) United States Patent
Dietz et al.

(10) Patent No.: US 9,137,996 B2
(45) Date of Patent: Sep. 22, 2015

(54) FUNGICIDAL ALKYL- AND ARYL-SUBSTITUTED 2[-2-CHLORO-4-(DIHALO-PHENOXY)-PHENYL]-1-[1,2,4]TRIAZOL-1-YL-ETHANOL COMPOUNDS

(75) Inventors: Jochen Dietz, Karlsruhe (DE); Richard Riggs, Mannheim (DE); Nadege Boudet, Hemsbach (DE); Jan Klaas Lohmann, Lambsheim (DE); Ian Robert Craig, Ludwigshafen (DE); Egon Haden, Speyer (DE); Erica May Wilson Lauterwasser, Mannheim (DE); Bernd Mueller, Frankenthal (DE); Wassilios Grammenos, Ludwigshafen (DE); Thomas Grote, Wachenheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/232,434

(22) PCT Filed: Jul. 12, 2012

(86) PCT No.: PCT/EP2012/063620
§ 371 (c)(1),
(2), (4) Date: Jan. 13, 2014

(87) PCT Pub. No.: WO2013/010885
PCT Pub. Date: Jan. 24, 2013

(65) Prior Publication Data
US 2014/0141973 A1 May 22, 2014

Related U.S. Application Data

(60) Provisional application No. 61/508,086, filed on Jul. 15, 2011.

(30) Foreign Application Priority Data

Jul. 15, 2011 (EP) .................................. 11174186

(51) Int. Cl.
| | |
|---|---|
| C07D 249/08 | (2006.01) |
| A01N 43/653 | (2006.01) |
| C07D 405/06 | (2006.01) |
| C07D 303/18 | (2006.01) |
| C07D 303/22 | (2006.01) |
| C07C 45/70 | (2006.01) |

(52) U.S. Cl.
CPC .............. *A01N 43/653* (2013.01); *C07C 45/70* (2013.01); *C07D 249/08* (2013.01); *C07D 303/18* (2013.01); *C07D 303/22* (2013.01); *C07D 405/06* (2013.01)

(58) Field of Classification Search
CPC ...................................................... C07D 249/08
USPC ...................................... 504/272; 548/262.2
See application file for complete search history.

(56) References Cited

U.S. PATENT DOCUMENTS

| | | | |
|---|---|---|---|
| 4,242,121 | A | 12/1980 | Hawkins et al. |
| 4,599,362 | A | 7/1986 | Nakatani et al. |
| 4,940,720 | A | 7/1990 | Nevill et al. |
| 4,945,100 | A | 7/1990 | Nyfeler et al. |
| 4,992,458 | A | 2/1991 | Riebli et al. |
| 5,143,932 | A | 9/1992 | Jautelat et al. |
| 5,162,358 | A | 11/1992 | Jautelat et al. |
| 2008/0108686 | A1 | 5/2008 | Gewehr et al. |
| 2009/0036509 | A1 | 2/2009 | Gewehr et al. |
| 2009/0286768 | A1 | 11/2009 | Crew et al. |

FOREIGN PATENT DOCUMENTS

| | | |
|---|---|---|
| AU | 611315 | 6/1991 |
| CA | 1100976 | 5/1981 |
| CA | 1209152 | 8/1986 |
| CN | 101225074 | 7/2008 |
| CS | 247 200 | 12/1986 |
| DE | 2 325 878 | 12/1974 |
| DE | 3801233 | 8/1988 |
| DE | 40 03 180 | 8/1991 |
| EP | 0 000 017 | 12/1978 |
| EP | 0 113 640 | 7/1984 |
| EP | 0 126 430 | 11/1984 |
| EP | 0 275 955 | 7/1988 |
| EP | 0 354 183 | 2/1990 |
| EP | 0 440 950 | 8/1991 |
| EP | 0 470 466 | 2/1992 |
| EP | 1 431 275 | 6/2004 |
| FR | 2 491 924 | 4/1982 |
| GB | 2 132 195 | 7/1984 |

(Continued)

OTHER PUBLICATIONS

Lima, 2005, Current Medicinal Chemistry, vol. 12, p. 23-49.*
International Search Report, PCT/EP2012/063620, issued Sep. 18, 2012.
International Preliminary Report on Patentability, PCT/EP2012/063620, issued Jan. 21, 2014.
Akama, Tsutomu, et al. "Discovery and structure-activity study of a novel benzoxaborole anti-inflammatory agent (AN2728) for the potential topical treatment of psoriasis and atopic dermatitis", Bioorganic & Medicinal Chemistry Letters, 2009, p. 2129-2132, vol. 19.

(Continued)

*Primary Examiner* — Rebecca Anderson
*Assistant Examiner* — Karen Cheng
(74) *Attorney, Agent, or Firm* — Brinks Gilson & Lione

(57) ABSTRACT

The present invention relates to alkyl- and aryl-substituted 2-[2-chloro-4-(dihalo-phenoxy)-phenyl]-1-[1,2,4]triazol-1-yl-ethanol compounds of formula I as defined in the description, and the N-oxides, and salts thereof, processes and intermediates for preparing these compounds and also to compositions comprising at least one such compound. The invention also relates to the use of such compounds and compositions for combating harmful fungi and seed coated with at least one such compound.

19 Claims, No Drawings

(56) References Cited

FOREIGN PATENT DOCUMENTS

| | | |
|---|---|---|
| WO | WO 96/41804 | 12/1996 |
| WO | WO 03 064572 | 8/2003 |
| WO | WO 2005/123689 | 12/2005 |
| WO | WO 2005/123690 | 12/2005 |
| WO | WO 2006/015866 | 2/2006 |
| WO | WO 2006/087373 | 8/2006 |
| WO | WO 2006/109933 | 10/2006 |
| WO | WO 2006/119876 | 11/2006 |
| WO | WO 2008/082198 | 7/2008 |
| WO | WO 2010/146114 | 12/2010 |
| WO | WO 2011/099804 | 8/2011 |
| WO | WO 2012/037782 | 3/2012 |
| WO | WO 2013/010862 | 1/2013 |
| WO | WO 2013/010894 | 1/2013 |
| WO | WO 2013/024076 | 1/2013 |
| WO | WO 2013/024077 | 1/2013 |
| WO | WO 2013/024082 | 1/2013 |
| WO | WO 2013007767 | 1/2013 |
| WO | WO 2013/024075 | 2/2013 |
| WO | WO 2013/024080 | 2/2013 |
| WO | WO 2013/024081 | 2/2013 |
| WO | WO 2013/024083 | 2/2013 |

OTHER PUBLICATIONS

Yu et al., "Synthesis and Fungicidal Evaluation of 2-arylphenyl ether-3-(1H-1,2,4-triazol-1-yl)propan-2-ol Derivatives," Journal of Agricultural and Food Chemistry, vol. 57, No. 11, (2009), pp. 4854-4860.

Office Action dated Dec. 10, 2014, issued in U.S. Appl. No. 14/237,463.

Office Action dated Dec. 8, 2014, issued in U.S. Appl. No. 14/232,462.

Office Action dated Dec. 8, 2014, issued in U.S. Appl. No. 14/237,048.

* cited by examiner

FUNGICIDAL ALKYL- AND ARYL-SUBSTITUTED 2[-2-CHLORO-4-(DIHALO-PHENOXY)-PHENYL]-1-[1,2,4]TRIAZOL-1-YL-ETHANOL COMPOUNDS

This application is a National Stage application of International Application No. PCT/EP2012/063620, filed Jul. 12, 2012, which claims the benefit of U.S. Provisional Application No. 61/508,086, filed Jul. 15, 2011. This application also claims priority under 35 U.S.C. §119 to EP Patent Application No. 11174186.4, filed Jul. 15, 2011.

The present invention relates to fungicidal alkyl- or aryl-substituted 2-[2-chloro-4-(dihalo-phenoxy)-phenyl]-1-[1,2,4]triazol-1-yl-ethanol compounds and the N-oxides and the salts thereof for combating phytopathogenic fungi, and to the use and methods for combating phytopathogenic fungi and to seeds coated with at least one such compound. The invention also relates to processes for preparing these compounds and to compositions comprising at least one such compound.

Certain alkyl- or aryl-substituted 2-[2-chloro-4-(4-halogen-phenoxy)-phenyl]-1-[1,2,4]triazol-1-yl-ethanol compounds of formula

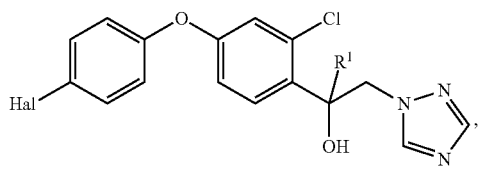

wherein $R^1$ is hydrogen, alkyl, halogenalkyl, halogenallyl or optionally substituted styryl, and their use for controlling phytopathogenic fungi are known from J. Agric. Food Chem. (2009) 57, 4854-4860, EP 0 113 640 A2, EP 0 275 955 A1, EP 0 470 466 A2, DE 40 03 180 A1 and CN 101225074 A. WO 2010/146114 relates to triazole compounds carrying a sulfur substituent according to formulae I and II as defined in WO 2010/146114 and inter alia to intermediate compounds IV, their use as fungicides and production methods:

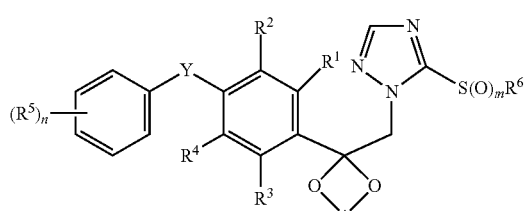

(I)

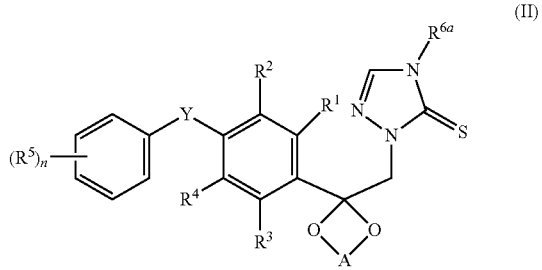

(II)

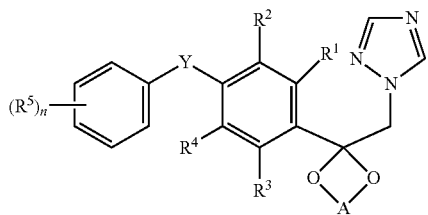

(IV)

EP 0 126 430 relates to a process for preparing certain 1-triazolyletherether-derivatives.

The compounds according to the present invention differ from those described in the abovemention publications inter alia by adding at least one further halogen substituent in ortho-position to the phenoxy group as defined herein.

In many cases, in particular at low application rates, the fungicidal activity of the known fungicidal compounds is unsatisfactory. Based on this, it was an object of the present invention to provide compounds having improved activity and/or a broader activity spectrum against phytopathogenic harmful fungi.

This object is achieved by alkyl- and aryl-substituted 2-[2-chloro-4-(dihalo-phenoxy)phenyl]-1-[1,2,4]triazol-1-yl-ethanol compounds having good fungicidal activity against phytopathogenic harmful fungi.

Accordingly, the present invention relates to the compounds of formula I:

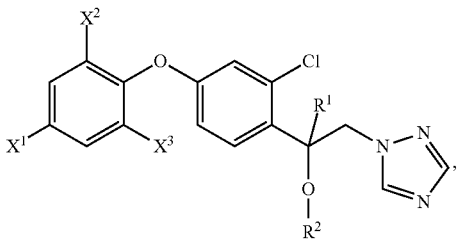

wherein:
$X^1,X^2$ independently of each other are selected from halogen;
$X^3$ is hydrogen or halogen;
$R^1,R^2$ independently of each other are hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, phenyl, phenyl-$C_1$-$C_4$-alkyl, phenyl-$C_2$-$C_4$-alkenyl or phenyl-$C_2$-$C_4$-alkynyl,
wherein the aliphatic groups $R^1$ and/or $R^2$ may carry 1, 2, 3 or up to the maximum possible number of identical or different groups $R^a$ which independently of one another are selected from:
$R^a$ halogen, CN, nitro, $C_1$-$C_4$-alkoxy and $C_1$-$C_4$-halogenalkoxy;
wherein the cycloalkyl and/or phenyl moieties of $R^1$ and/or $R^2$ may carry 1, 2, 3, 4, 5 or up to the maximum number of identical or different groups $R^b$ which independently of one another are selected from:
$R^b$ halogen, CN, nitro, $C_1$-$C_4$-alkyl, $C_1$-$C_4$-alkoxy, $C_1$-$C_4$-halogenalkyl and $C_1$-$C_4$-halogenalkoxy;
and the N-oxides and the agriculturally acceptable salts thereof.

The present invention furthermore relates to the use of these compounds for combating harmful fungi and seed coated with at least one such compound and also to compositions comprising at least one such compound of formula I.

The present invention furthermore relates to processes for preparing compounds of formula I and to intermediates such as compounds of formulae IV, V, Va, VII and XI.

The term "compounds I" refers to compounds of formula I. Likewise, this terminology applies to all sub-formulae, e.g. "compounds I.A" refers to compounds of formula I.A or "compounds XI" refers to compounds of formula XI, etc.

The compounds I can be obtained by various routes in analogy to prior art processes known (cf. J. Agric. Food Chem. (2009) 57, 4854-4860; EP 0 275 955 A1; DE 40 03 180 A1; EP 0 113 640 A2; EP 0 126 430 A2) and by the synthesis routes shown in the following schemes and in the experimental part of this application.

In a first process, for example, halo-phenoles II wherein $X^1$, $X^2$ and $X^3$ are as defined herein, are reacted, in a first step, with derivatives IIIIc,

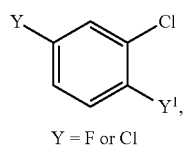

Y = F or Cl wherein $Y^1$ stands for I or Br, in particular bromo derivatives III, wherein Y is F or Cl, preferably in the presence of a base. in the presence of a base such as potassium carbonate, sodium hydroxide or sodium hydride to obtain compounds VII. These triazole compounds VII are reacted with a Grignard reagent $R^1$-M of formula VIII wherein $R^1$ is as defined above and M is MgBr, MgCl, Li or Na (e.g. phenylalkyl-MgBr or an organolithium reagent phenylalkyl-Li), preferably under anhydrous conditions to obtain compounds I wherein $R^2$ is hydrogen, which compounds are of formula I.A. Optionally, a Lewis acid such as $LaCl_3x2 LiCl$ or $MgBr_2xOEt_2$ can be used. If appropriate, these compounds I.A can subsequently be alkylated e.g. with $R^2$-LG, wherein LG represents a nucleophilically replaceable leaving group such as halogen, alkylsulfonyl, alkylsulfonyloxy and arylsulfonyloxy, preferably chloro, bromo or iodo, particularly preferably bromo, preferably in the presence of a base, such as for example, NaH in a suitable solvent such as THF, to form compounds I. The preparation of compounds I can be illustrated by the following scheme:

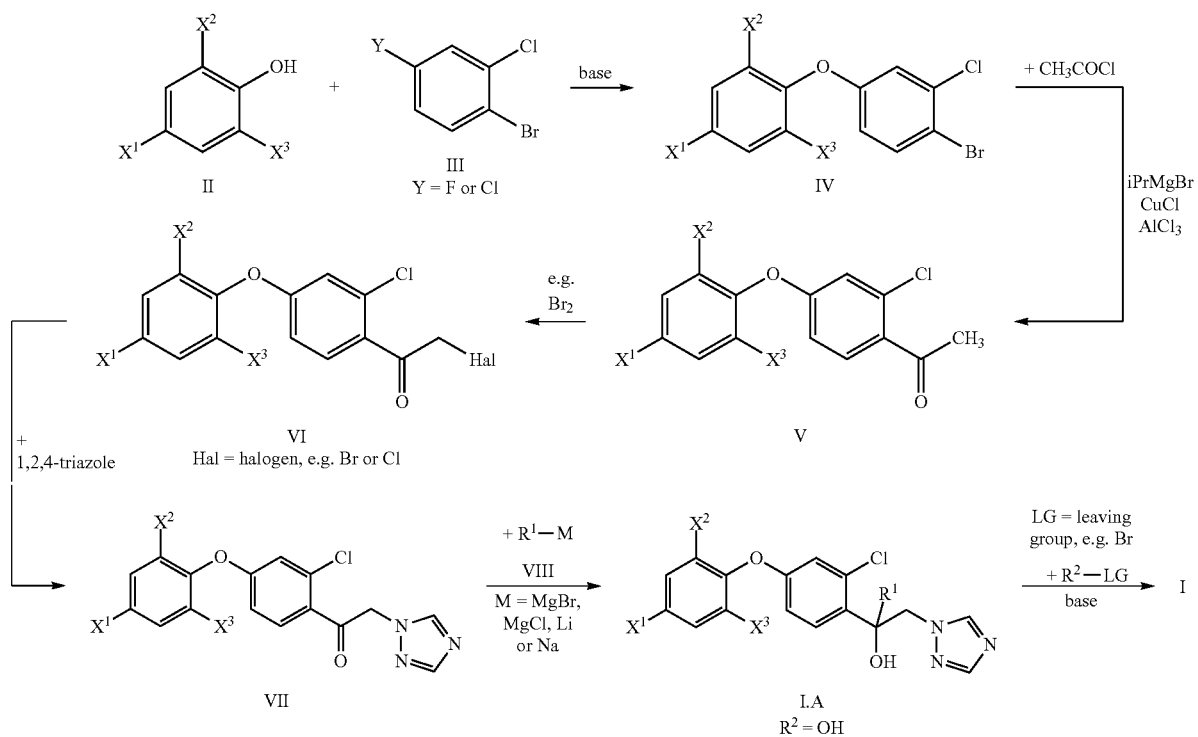

Thereafter, the resulting compounds IVa, in particular IV (wherein $Y^1$ is Br), are then transformed into Grignard reagents by the reaction with transmetallation reagents such as isopropylmagnesium halides and subsequently reacted with acetyl chloride preferably under anhydrous conditions and preferably in the presence of a catalyst such as CuCl, $AlCl_3$, LiCl and mixtures thereof, to obtain acetophenones V. These compounds V can be halogenated e.g. with bromine preferably in an organic solvent such as diethyl ether, methyl tert.-butyl ether (MTBE), methanol or acetic acid. The resulting compounds VI can subsequently reacted with 1H-1,2,4-triazole preferably in the presence of a solvent such as tetrahydrofuran (THF), dimethylormamide (DMF), toluene and In a second process to obtain compounds I, bromo derivatives III, in a first step, are reacted with e.g. isopropylmagnesium bromide followed by an acyl chloride agent IX wherein $R^1$ is as defined above (e.g. acetyl chloride) preferably under anhydrous conditions and optionally in the presence of a catalyst such as CuCl, $AlCl_3$, LiCl and mixtures thereof, to obtain compounds X. Alternatively, 1,3-dichlorobenzene of formula IIIb can be reacted with an acyl chloride agent IX wherein $R^1$ is as defined above (e.g. acetyl chloride) preferably in the presence of a catalyst such as $AlCl_3$. Then, ketones X are reacted with phenoles II preferably in the presence of a base to obtain compounds Va.

Thereafter, intermediates Va are reacted with trimethylsulf(ox)onium halides, preferably iodide preferably in the presence of a base such as sodium hydroxide. Thereafter, the epoxides XI are reacted with 1H-1,2,4-triazole preferably in the presence of a base such as potassium carbonate and preferably in the presence of an organic solvent such as DMF to obtain compounds I A, which can subsequently be alkylated as described above. The preparation of compounds I.A can be illustrated by the following scheme:

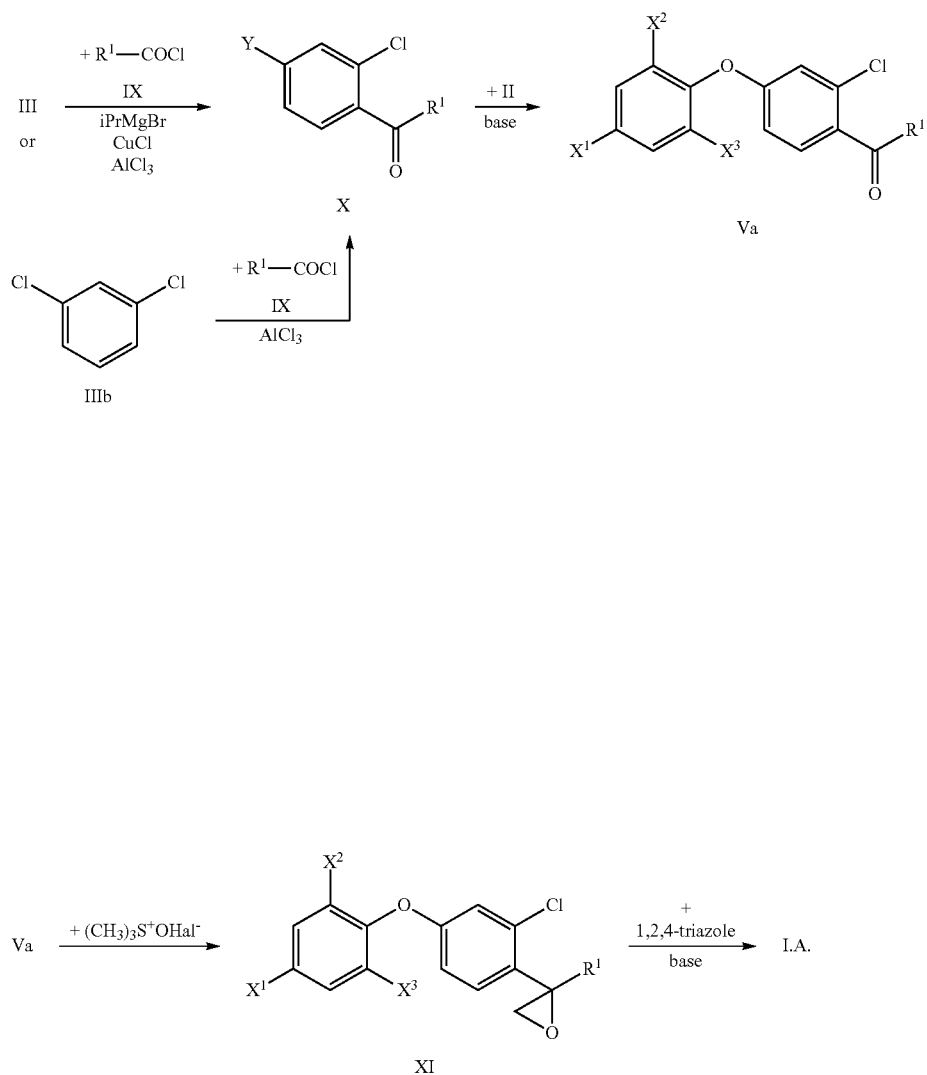

In a third process, the epoxide ring of intermediates XI which may be obtained according to the second process described herein is cleaved by reaction with alcohols $R^2OH$ preferably under acidic conditions. Thereafter, the resulting compounds XII are reacted with halogenating agents or sulfonating agents such as $PBr_3$, $PCl_3$, mesyl chloride, tosyl chloride or thionyl chloride to obtain compounds XIII wherein LG is a nucleophilically replaceable leaving group such as halogen, alkylsulfonyl, alkylsulfonyloxy and arylsulfonyloxy, preferably chloro, bromo or iodo, particularly preferably bromo or alkylsulfonyl. Then compounds XIII are reacted with 1H-1,2,4-triazole to obtain compounds I. The preparation of compounds I can be illustrated by the following scheme:

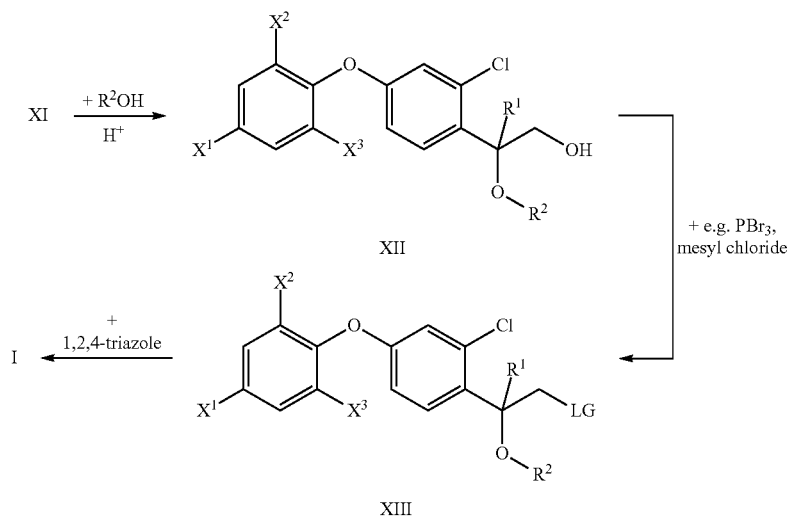

If individual compounds I cannot be obtained by the routes described above, they can be prepared by derivatization of other compounds I.

The N-oxides may be prepared from the compounds I according to conventional oxidation methods, e.g. by treating compounds I with an organic peracid such as metachloroperbenzoic acid (cf. WO 03/64572 or J. Med. Chem. 38(11), 1892-903, 1995); or with inorganic oxidizing agents such as hydrogen peroxide (cf. J. Heterocyc. Chem. 18(7), 1305-8, 1981) or oxone (cf. J. Am. Chem. Soc. 123(25), 5962-5973, 2001). The oxidation may lead to pure mono-N-oxides or to a mixture of different N-oxides, which can be separated by conventional methods such as chromatography.

If the synthesis yields mixtures of isomers, a separation is generally not necessarily required since in some cases the individual isomers can be interconverted during workup for use or during application (e.g. under the action of light, acids or bases). Such conversions may also take place after use, e.g. in the treatment of plants in the treated plant, or in the harmful fungus to be controlled.

In the following, the intermediate compounds are further described. A skilled person will readily understand that the preferences for the substituents given herein in connection with compounds I apply for the intermediates accordingly. Thereby, the substituents in each case have independently of each other or more preferably in combination the meanings as defined herein.

At least part of compounds of formula IVa and IV are novel. Consequently, a further embodiment of the present invention are compounds of formula IVa

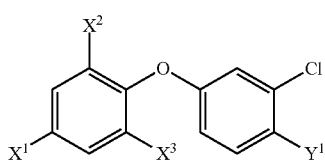

wherein the variables $X^1$, $X^2$, $X^3$ are as defined and preferably defined for formula I herein, and wherein $Y^1$ stands for I or Br.

According to one embodiment of formula IVa, $Y^1$ is I. According to another embodiment of formula IVa, $Y^1$ is Br, corresponding to formula IV.

According to one preferred embodiment, in compounds IV and IVa $X^1$ is F.

In specific embodiments of compounds IV and IVa according to the present invention, the substituents $X^1$, $X^2$, $X^3$ are as defined in tables 1 to 160 below for compounds I.

At least part of compounds of formula Va and V are novel. Consequently, a further embodiment of the present invention are compounds of formula V and Va

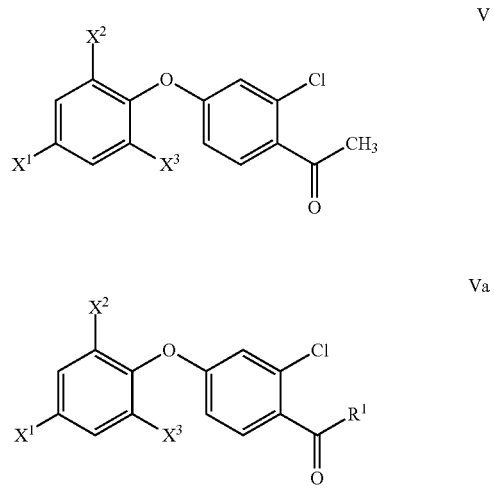

wherein the variables $X^1$, $X^2$, $X^3$ and $R^1$ are as defined and preferably defined for formula I herein.

According to one embodiment of formula IVa, $R^1$ is $CH_3$, corresponding to formula V.

According to one preferred embodiment, in compounds V and Va $X^1$ is F.

In specific embodiments of compounds IV and IVa according to the present invention, the substituents $X^1$, $X^2$, $X^3$ are as defined in tables 1 to 160 below for compounds I.

At least part of compounds of formula VI are novel. Consequently, a further embodiment of the present invention are compounds of formula VI

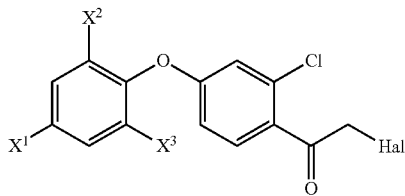

VI wherein the variables $X^1, X^2, X^3$ are as defined and preferably defined for formula I herein and wherein Hal stands for halogen, in particular Br or Cl.

According to one preferred embodiment, in compounds VI $X^1$ is F.

In specific embodiments of compounds VI according to the present invention, the substituents $X^1, X^2, X^3$ are as defined in tables 1 to 160 below for compounds I.

Compounds of formula VII are novel. Consequently, a further embodiment of the present invention are compounds of formula VII

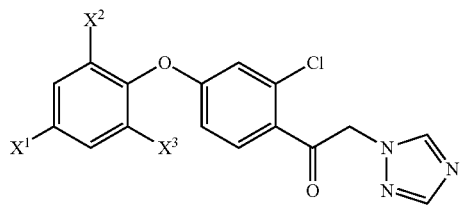

VII wherein the variables $X^1, X^2, X^3$ are as defined and preferably defined for formula I herein.

According to one preferred embodiment, in compounds VII $X^1$ is F.

In specific embodiments of compounds VII according to the present invention, the substituents $X^1$, $X^2$, $X^3$ are as defined in tables 1 to 160 below for compounds I.

Compounds of formula XI are novel. Consequently, a further embodiment of the present invention are compounds of formula XI

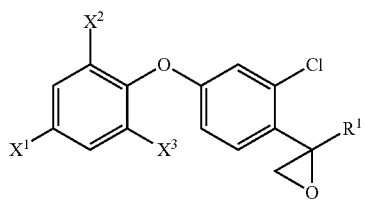

XI wherein the variables $X^1$, $X^2$, $X^3$ and $R^1$ are as defined and preferably defined for formula I herein.

According to one preferred embodiment, in compounds XI $X^1$ is F.

In specific embodiments of compounds XI according to the present invention, the substituents $X^1$, $X^2$, $X^3$ and $R^1$ are as defined in tables 1 to 160 below for compounds I.

Compounds of formula XII are novel. Consequently, a further embodiment of the present invention are compounds of formula XII

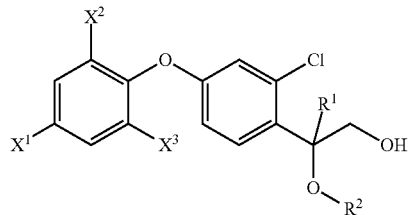

XII wherein the variables $X^1, X^2, X^3, R^1$ and $R^2$ are as defined and preferably defined for formula I herein.

According to one preferred embodiment, in compounds XII $X^1$ is F.

In specific embodiments of compounds XII according to the present invention, the substituents $X^1, X^2, X^3, R^1$ and $R^2$ are as defined in tables 1 to 160 below for compounds I.

Compounds of formula XIII are novel. Consequently, a further embodiment of the present invention are compounds of formula XIII

XIII wherein the variables $X^1, X^2, X^3, R^1$ and $R^2$ are as defined and preferably defined for formula I herein and LG stands for a leaving group as defined above.

According to one preferred embodiment, in compounds XIII $X^1$ is F.

In specific embodiments of compounds XIII according to the present invention, the substituents $X^1, X^2, X^3, R^1$ and $R^2$ are as defined in tables 1 to 160 below for compounds I.

In the definitions of the variables given above, collective terms are used which are generally representative for the substituents in question. The term "$C_n$—$C_m$" indicates the number of carbon atoms possible in each case in the substituent or substituent moiety in question.

The term "halogen" refers to fluorine, chlorine, bromine and iodine.

The term "$C_1$-$C_6$-alkyl" refers to a straight-chained or branched saturated hydrocarbon group having 1 to 6 carbon atoms, e.g. methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Likewise, the term "$C_2$-$C_4$-alkyl" refers to a straight-chained or branched alkyl group having 2 to 4 carbon atoms, such as ethyl, propyl (n-propyl), 1-methylethyl (iso-propoyl), butyl, 1-methylpropyl (sec.-butyl), 2-methylpropyl (iso-butyl), 1,1-dimethylethyl (tert.-butyl).

The term "$C_2$-$C_4$-alkenyl" refers to a straight-chain or branched unsaturated hydrocarbon radical having 2 to 4 carbon atoms and a double bond in any position, e.g. ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl. Likewise, the term "$C_2$-$C_6$-alkenyl" refers to a straight-chain or branched unsaturated hydrocarbon radical having 2 to 6 carbon atoms and a double bond in any position.

The term "$C_2$-$C_4$-alkynyl" refers to a straight-chain or branched unsaturated hydrocarbon radical having 2 to 4 carbon atoms and containing at least one triple bond, such as ethynyl, prop-1-ynyl, prop-2-ynyl (propargyl), but-1-ynyl, but-2-ynyl, but-3-ynyl, 1-methyl-prop-2-ynyl. Likewise, the term "$C_2$-$C_6$-alkynyl" refers to a straight-chain or branched unsaturated hydrocarbon radical having 2 to 6 carbon atoms and at least one triple bond.

The term "$C_1$-$C_4$-halogenalkyl" refers to a straight-chained or branched alkyl group having 1 to 4 carbon atoms, wherein some or all of the hydrogen atoms in these groups may be replaced by halogen atoms as mentioned above, for example chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2$—$C_2F_5$, $CF_2$—$C_2F_5$, $CF(CF_3)_2$, 1-fluoromethyl-2-fluoroethyl, 1-(chloromethyl)-2-chloroethyl, 1-bromomethyl-2-bromoethyl, 4-fluorobutyl, 4-chlorobutyl, 4-bromobutyl or nonafluorobutyl, and the like.

The term "$C_3$-$C_8$-cycloalkyl" refers to monocyclic saturated hydrocarbon radicals having 3 to 8 carbon ring members, such as cyclopropyl, cyclobutyl, cyclopentyl, cyclohexyl, cycloheptyl or cyclooctyl.

The term "$C_3$-$C_8$-cycloalkyl-$C_1$-$C_4$-alkyl" refers to alkyl having 1 to 4 carbon atoms (as defined above), wherein one hydrogen atom of the alkyl radical is replaced by a cycloalkyl radical having 3 to 8 carbon atoms (as defined above).

The term "$C_1$-$C_4$-alkoxy" refers to a straight-chain or branched alkyl group having 1 to 4 carbon atoms which is bonded via an oxygen, at any position in the alkyl group, e.g. methoxy, ethoxy, n-propoxy, 1-methylethoxy, butoxy, 1-methyl-propoxy, 2-methylpropoxy or 1,1-dimethylethoxy.

The term "$C_1$-$C_4$-halogenalkoxy" refers to a $C_1$-$C_4$-alkoxy radical as defined above, wherein some or all of the hydrogen atoms in these groups may be replaced by halogen atoms as mentioned above, e.g., $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoro-propoxy, 2 chloropropoxy, 3-chloropropoxy, 2,3-dichloropropoxy, 2-bromopropoxy, 3 bromopropoxy, 3,3,3-trifluoropropoxy, 3,3,3-trichloropropoxy, $OCH_2$—$C_2F_5$, $OCF_2$—$C_2F_5$, 1-fluoromethyl-2-fluoroethoxy, 1-chloromethyl-2-chloroethoxy, 1-bromomethyl-2-bromo-ethoxy, 4-fluorobutoxy, 4-chlorobutoxy, 4-bromobutoxy or nonafluorobutoxy.

The term "phenyl-$C_1$-$C_4$-alkyl" refers to alkyl having 1 to 4 carbon atoms (as defined above), wherein one hydrogen atom of the alkyl radical is replaced by a phenyl radical. Likewise, the terms "phenyl-$C_2$-$C_4$-alkenyl" and "phenyl-$C_2$-$C_4$-alkynyl" refer to alkenyl and alkynyl, respectively, wherein one hydrogen atom of the aforementioned radicals is replaced by a phenyl radical.

Agriculturally acceptable salts of compounds I encompass especially the salts of those cations or the acid addition salts of those acids whose cations and anions, respectively, have no adverse effect on the fungicidal action of the compounds I. Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may carry one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium. Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formula I with an acid of the corresponding anion, preferably of hydrochloric acid, hydrobromic acid, sulfuric acid, phosphoric acid or nitric acid.

The compounds of formula I can be present in atropisomers arising from restricted rotation about a single bond of asymmetric groups. They also form part of the subject matter of the present invention.

Depending on the substitution pattern, the compounds of formula I and their N-oxides may have one or more centers of chirality, in which case they are present as pure enantiomers or pure diastereomers or as enantiomer or diastereomer mixtures. Both, the pure enantiomers or diastereomers and their mixtures are subject matter of the present invention.

In respect of the variables, the embodiments of the intermediates correspond to the embodiments of the compounds I.

Preference is given to those compounds I and where applicable also to compounds of all sub-formulae such as I.1, I.A, I.B, I.C etc., provided herein and to the intermediates such as compounds IV, V, Va, VII, IX or XI etc., wherein the substituents (such as $X^1$, $X^2$, $X^3$, $R^1$, $R^2$, $R^a$ and $R^b$) have independently of each other or more preferably in combination the following meanings:

One embodiment relates to compounds I, wherein $X^1$ is F.

According to a further embodiment, $X^1$ is Cl.

Another embodiment relates to compounds I, wherein $X^2$ is F.

According to a further embodiment, $X^2$ is Cl.

A further embodiment relates to compounds I, wherein $X^3$ is hydrogen.

According to still a further embodiment, $X^3$ is F or Cl.

A further embodiment relates to compounds I, wherein the substitution of the phenoxy moiety

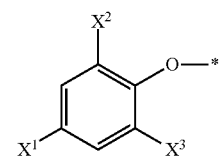

by the combination of $X^1$, $X^2$ and $X^3$ is selected from 2,4-$Cl_2$, 2,4-$F_2$, 2-F-4-Cl, 4-F-2-Cl, 2,4,6-$Cl_3$, 2,4,6-$F_3$, 2,6-$F_2$-4-Cl and 4-F-2,6-$Cl_2$.

Particularly preferred embodiments of the invention relate to compounds I, wherein the combination of $X^1$, $X^2$ and $X^3$ is as defined in Table p below.

TABLE P

| line | $X^1$ | $X^2$ | $X^3$ |
|------|-------|-------|-------|
| P-1 | Cl | Cl | H |
| P-2 | Cl | F | H |
| P-3 | F | Cl | H |
| P-4 | Cl | Cl | Cl |
| P-5 | Cl | F | F |
| P-6 | F | Cl | Cl |
| P-7 | F | F | F |
| P-8 | F | F | H |

According to one embodiment, $R^1$ is H.

According to a further embodiment of the invention, $R^1$ is selected from $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, phenyl, phenyl-$C_1$-$C_4$-alkyl, phenyl-$C_2$-$C_4$-alkenyl and phenyl-$C_2$-$C_4$-alkynyl, wherein the aliphatic groups of $R^1$ are in each case unsubstituted or carry 1, 2, 3 or up to the maximum possible number of identical or different groups $R^a$, and the cycloalkyl and/or phenyl moieties of $R^1$ are in each case unsubstituted or carry 1, 2, 3, 4, 5 or up to the maximum number of identical or different groups $R^b$.

According to one embodiment, $R^1$ is $C_1$-$C_6$-alkyl. According to a specific embodiment thereof, $R^1$ is $C_1$-$C_2$-alkyl, in particular $CH_3$. According to another embodiment, $R^1$ is $C_2$-$C_6$-alkenyl. According to still another embodiment, $R^1$ is $C_2$-$C_6$-alkynyl. According to still another embodiment, $R^1$ is $C_3$-$C_8$-cycloalkyl. According to still another embodiment, $R^1$ is $C_3$-$C_8$-cycloalkyl-$C_1$-$C_4$-alkyl. According to still another embodiment, $R^1$ is phenyl. According to still another embodiment, $R^1$ is phenyl-$C_1$-$C_4$-alkyl. In everyone of these embodiments, $R^1$ is unsubstituted or substituted by 1 to 3 $R^a$ selected from halogen, in particular F and $C_1$, $C_1$-$C_4$-alkoxy and CN and/or 1 to 3 $R^b$ selected from halogen, in particular Cl and F, $C_1$-$C_4$-alkoxy, $C_1$-$C_4$-alkyl and CN. According to one specific embodiment, $R^1$ is $C_1$-$C_6$-alkyl that is substituted by 1, 2 or 3 halogen, in particular selected from Cl and F. According to a specific embodiment thereof, $R^1$ is $C_1$-$C_2$-alkyl, substituted by 1 to 2 halogen, in particular selected from F and Cl, in particular $CF_3$ or $CHF_2$. Another embodiment relates to compounds I, wherein $R^1$ is selected from hydrogen, $C_1$-$C_4$-alkyl, allyl, $C_2$-$C_6$-alkynyl, cyclopropyl, cyclopropylmethyl, phenyl, benzyl, phenylethenyl and phenylethinyl.

A further embodiment relates to compounds I, wherein $R^1$ is selected from $C_1$-$C_4$-alkyl, allyl, $C_2$-$C_6$-alkynyl, cyclopropyl, cyclopropylmethyl, phenyl, benzyl, phenylethenyl and phenylethinyl, wherein the aforementioned groups carry 1, 2 or 3 halogen substituents, more preferably $R^1$ is $C_1$-$C_2$-haloalkyl, in particular $R^1$ is $CF_3$.

A further embodiment relates to compounds I, wherein $R^1$ is $C_3$-$C_8$-cycloalkyl or $C_3$-$C_8$-cycloalkyl-$C_1$-$C_4$-alkyl, more preferably selected from cyclopropyl and cyclopropylmethyl.

Particularly preferred embodiments of the invention relate to compounds I, wherein $R^1$ is as defined in Table A and Table A-2 below.

According to one embodiment, $R^2$ is hydrogen (compounds of formula I.A).

According to a further embodiment, $R^2$ is selected from $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, phenyl, phenyl-$C_1$-$C_4$-alkyl, phenyl-$C_2$-$C_4$-alkenyl and phenyl-$C_2$-$C_4$-alkynyl, wherein the aliphatic groups of $R^2$ are in each case unsubstituted or carry 1, 2, 3 or up to the maximum possible number of identical or different groups $R^a$, and the cycloalkyl and/or phenyl moieties of $R^2$ are in each case unsubstituted or carry 1, 2, 3, 4, 5 or up to the maximum number of identical or different groups $R^b$.

According to one specific embodiment, $R^2$ is $C_1$-$C_6$-alkyl. According to one further specific embodiment, $R^2$ is $C_2$-$C_6$-alkenyl, in particular allyl. According to one further specific embodiment, $R^2$ is $C_2$-$C_6$-alkynyl, in particular propargyl or methylpropargyl.

According to one further specific embodiment, $R^2$ is phenyl. According to one further specific embodiment, $R^2$ is phenyl-$C_1$-$C_4$-alkyl, in particular benzyl. In everyone of these embodiments, $R^2$ is unsubstituted or substituted by 1 to 3 $R^a$ selected from halogen, in particular F and Cl, $C_1$-$C_4$-alkoxy and/or 1 to 3 $R^b$ selected from halogen, in particular Cl and F, $C_1$-$C_4$-alkoxy and $C_1$-$C_4$-alkyl. One specific embodiment further relates to compounds wherein $R^2$ is $C_1$-$C_4$-alkoxy-$C_1$-$C_6$-alkyl.

A further embodiment relates to compounds I, wherein $R^2$ is selected from hydrogen, $C_1$-$C_4$-alkyl, allyl, propargyl and benzyl, in particular $R^2$ is hydrogen, which compounds are of formula I.A.

A further embodiment relates to compounds I, wherein $R^2$ is methyl, which compounds are of formula I.B:

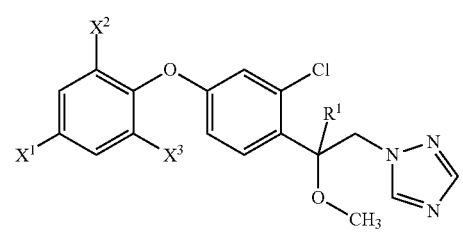

I.B

A further embodiment relates to compounds I, wherein $R^2$ is ethyl, which compounds are of formula I.C:

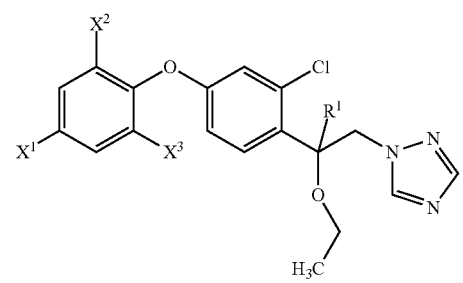

I.C

A further embodiment relates to compounds I, wherein $R^2$ is isopropyl which compounds are of formula I.D and still a further embodiment relates to compounds I, wherein $R^2$ is benzyl which compounds are of formula I.E:

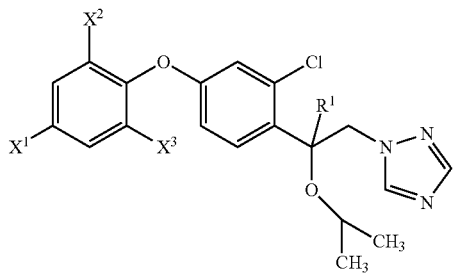

I.D

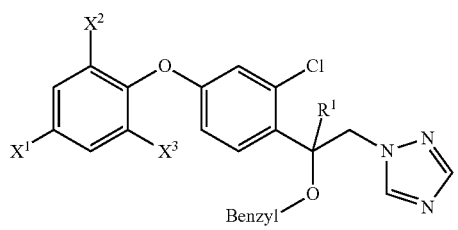

I.E

A further embodiment relates to compounds I, wherein $R^2$ is $CH_2$—$OCH_3$ which compounds are of formula I.F, and still a further embodiment relates to compounds I, wherein $R^2$ is allyl which compounds are of formula I.G:

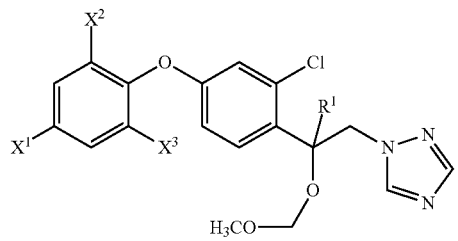

I.F

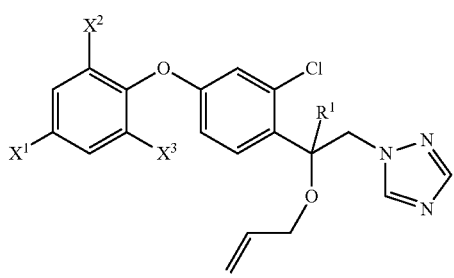

I.G

A further embodiment relates to compounds I, wherein $R^2$ is n-propyl which compounds are of formula I.H, and still a further embodiment relates to compounds I, wherein $R^2$ is propargyl which compounds are of formula I.J:

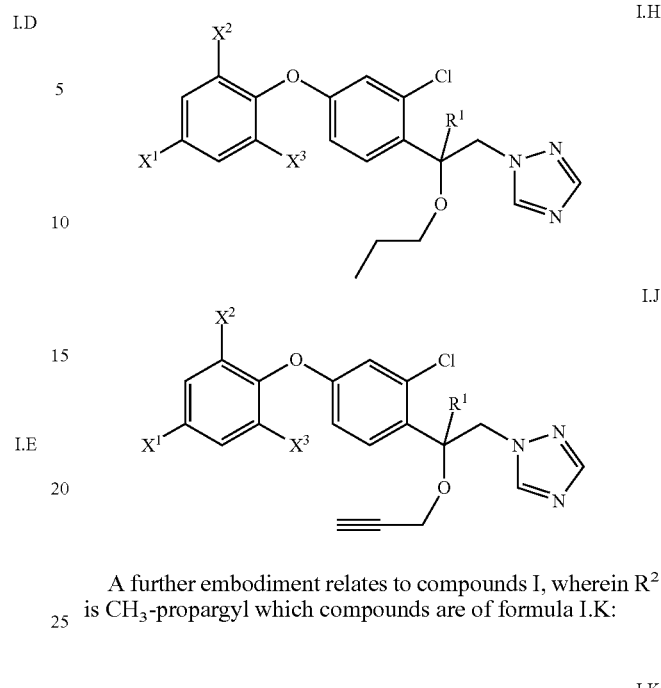

A further embodiment relates to compounds I, wherein $R^2$ is $CH_3$-propargyl which compounds are of formula I.K:

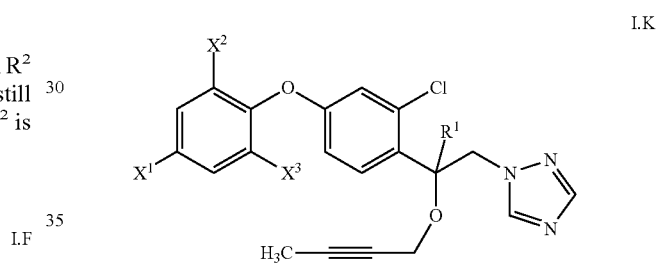

I.K

A skilled person will readily understand that the preferences given in connection with compounds I apply for formulae IV, V, Va, VI, VII, XI, XII and XIII as defined above.

With respect to their use, particular preference is given to the compounds of formulae I.A, I.B, I.C, I.D, I.E, I.F, I.G, I.H, I.J and I.K compiled in Tables 1 to 160 below. The groups mentioned in the Tables for a substituent are furthermore, independently of the combination wherein they are mentioned, a particularly preferred embodiment of the substituent in question.

Table 1: Compounds I to 30 of formula I.A, wherein $X^1$, $X^2$ and $X^3$ are defined as in line P-1 of table P and the meaning of $R^1$ for each individual compound corresponds in each case to one line of table A.

Table 2: Compounds 31 to 60 of formula I.A, wherein $X^1$, $X^2$ and $X^3$ are defined as in line P-2 of table P and the meaning of $R^1$ for each individual compound corresponds in each case to one line of table A.

Table 3: Compounds 61 to 90 of formula I.A, wherein $X^1$, $X^2$ and $X^3$ are defined as in line P-3 of table P and the meaning of $R^1$ for each individual compound corresponds in each case to one line of table A.

Table 4: Compounds 91 to 120 of formula I.A, wherein $X^1$, $X^2$ and $X^3$ are defined as in line P-4 of table P and the meaning of $R^1$ for each individual compound corresponds in each case to one line of table A.

Table 5: Compounds 121 to 150 of formula I.A, wherein $X^1$, $X^2$ and $X^3$ are defined as in line P-5 of table P and the meaning of $R^1$ for each individual compound corresponds in each case to one line of table A.

Table 6: Compounds 151 to 180 of formula I.A, wherein $X^1$, $X^2$ and $X^3$ are defined as in line P-6 of table P and the meaning of $R^1$ for each individual compound corresponds in each case to one line of table A.

Table 7: Compounds 181 to 210 of formula I.A, wherein $X^1$, $X^2$ and $X^3$ are defined as in line P-7 of table P and the meaning of $R^1$ for each individual compound corresponds in each case to one line of table A.

Tables 8 to 14: Compounds 211 to 420 of formula I.B, wherein $X^1$, $X^2$ and $X^3$ are defined as in Tables 1 to 7 and the meaning of $R^1$ for each individual compound corresponds in each case to one line of table A.

Consequently, this corresponds to:

Table 8: Compounds 211 to 240 of formula I.B, wherein $X^1$, $X^2$ and $X^3$ are defined as in line P-1 of table P and the meaning of $R^1$ for each individual compound corresponds in each case to one line of table A.

Table 9: Compounds 241 to 270 of formula I.B, wherein $X^1$, $X^2$ and $X^3$ are defined as in line P-2 of table P and the meaning of $R^1$ for each individual compound corresponds in each case to one line of table A.

Table 10: Compounds 271 to 300 of formula I.B, wherein $X^1$, $X^2$ and $X^3$ are defined as in line P-3 of table P and the meaning of $R^1$ for each individual compound corresponds in each case to one line of table A.

Table 11: Compounds 301 to 330 of formula I.B, wherein $X^1$, $X^2$ and $X^3$ are defined as in line P-4 of table P and the meaning of $R^1$ for each individual compound corresponds in each case to one line of table A.

Table 12: Compounds 331 to 360 of formula I.B, wherein $X^1$, $X^2$ and $X^3$ are defined as in line P-5 of table P and the meaning of $R^1$ for each individual compound corresponds in each case to one line of table A.

Table 13: Compounds 361 to 390 of formula I.B, wherein $X^1$, $X^2$ and $X^3$ are defined as in line P-6 of table P and the meaning of $R^1$ for each individual compound corresponds in each case to one line of table A.

Table 14: Compounds 391 to 420 of formula I.B, wherein $X^1$, $X^2$ and $X^3$ are defined as in line P-7 of table P and the meaning of $R^1$ for each individual compound corresponds in each case to one line of table A.

Tables 15 to 21: Compounds 421 to 630 of formula I.C, wherein $X^1$, $X^2$ and $X^3$ are defined as in Tables 1 to 7 and the meaning of $R^1$ for each individual compound corresponds in each case to one line of table A.

Consequently, this corresponds to:

Table 15: Compounds 421 to 450 of formula I.C, wherein $X^1$, $X^2$ and $X^3$ are defined as in line P-1 of table P and the meaning of $R^1$ for each individual compound corresponds in each case to one line of table A.

Table 16: Compounds 451 to 480 of formula I.C, wherein $X^1$, $X^2$ and $X^3$ are defined as in line P-2 of table P and the meaning of $R^1$ for each individual compound corresponds in each case to one line of table A.

Table 17: Compounds 481 to 510 of formula I.C, wherein $X^1$, $X^2$ and $X^3$ are defined as in line P-3 of table P and the meaning of $R^1$ for each individual compound corresponds in each case to one line of table A.

Table 18: Compounds 511 to 540 of formula I.C, wherein $X^1$, $X^2$ and $X^3$ are defined as in line P-4 of table P and the meaning of $R^1$ for each individual compound corresponds in each case to one line of table A.

Table 19: Compounds 541 to 570 of formula I.C, wherein $X^1$, $X^2$ and $X^3$ are defined as in line P-5 of table P and the meaning of $R^1$ for each individual compound corresponds in each case to one line of table A.

Table 20: Compounds 571 to 600 of formula I.C, wherein $X^1$, $X^2$ and $X^3$ are defined as in line P-6 of table P and the meaning of $R^1$ for each individual compound corresponds in each case to one line of table A.

Table 21: Compounds 601 to 630 of formula I.C, wherein $X^1$, $X^2$ and $X^3$ are defined as in line P-7 of table P and the meaning of $R^1$ for each individual compound corresponds in each case to one line of table A.

Table 22: Compounds 631 to 660 of formula I.A, wherein $X^1$, $X^2$ and $X^3$ are defined as in line P-8 of table P and the meaning of $R^1$ for each individual compound corresponds in each case to one line of table A.

Table 23: Compounds 661 to 690 of formula I.B, wherein $X^1$, $X^2$ and $X^3$ are defined as in line P-8 of table P and the meaning of $R^1$ for each individual compound corresponds in each case to one line of table A.

Table 24: Compounds 691 to 720 of formula I.C, wherein $X^1$, $X^2$ and $X^3$ are defined as in line P-8 of table P and the meaning of $R^1$ for each individual compound corresponds in each case to one line of table A.

Table 25 Compounds 721 to 750 of formula I.D, wherein $X^1$, $X^2$ and $X^3$ are defined as in line P-1 of table P and the meaning of $R^1$ for each individual compound corresponds in each case to one line of table A.

Table 26 Compounds 751 to 780 of formula I.D, wherein $X^1$, $X^2$ and $X^3$ are defined as in line P-2 of table P and the meaning of $R^1$ for each individual compound corresponds in each case to one line of table A.

Table 27 Compounds 781 to 810 of formula I.D, wherein $X^1$, $X^2$ and $X^3$ are defined as in line P-3 of table P and the meaning of $R^1$ for each individual compound corresponds in each case to one line of table A.

Table 28 Compounds 811 to 840 of formula I.D, wherein $X^1$, $X^2$ and $X^3$ are defined as in line P-4 of table P and the meaning of $R^1$ for each individual compound corresponds in each case to one line of table A.

Table 29 Compounds 841 to 870 of formula I.D, wherein $X^1$, $X^2$ and $X^3$ are defined as in line P-5 of table P and the meaning of $R^1$ for each individual compound corresponds in each case to one line of table A.

Table 30 Compounds 871 to 900 of formula I.D, wherein $X^1$, $X^2$ and $X^3$ are defined as in line P-6 of table P and the meaning of $R^1$ for each individual compound corresponds in each case to one line of table A.

Table 31 Compounds 901 to 930 of formula I.D, wherein $X^1$, $X^2$ and $X^3$ are defined as in line P-7 of table P and the meaning of $R^1$ for each individual compound corresponds in each case to one line of table A.

Table 32 Compounds 931 to 960 of formula I.D, wherein $X^1$, $X^2$ and $X^3$ are defined as in line P-8 of table P and the meaning of $R^1$ for each individual compound corresponds in each case to one line of table A.

Table 33 Compounds 961 to 990 of formula I.E, wherein $X^1$, $X^2$ and $X^3$ are defined as in line P-1 of table P and the meaning of $R^1$ for each individual compound corresponds in each case to one line of table A.

Table 34 Compounds 991 to 1020 of formula I.E, wherein $X^1$, $X^2$ and $X^3$ are defined as in line P-2 of table P and the meaning of $R^1$ for each individual compound corresponds in each case to one line of table A.

Table 35 Compounds 1021 to 1050 of formula I.E, wherein $X^1$, $X^2$ and $X^3$ are defined as in line P-3 of table P and the meaning of $R^1$ for each individual compound corresponds in each case to one line of table A.

Table 36 Compounds 1051 to 1080 of formula I.E, wherein $X^1$, $X^2$ and $X^3$ are defined as in line P-4 of table P and the meaning of $R^1$ for each individual compound corresponds in each case to one line of table A.

Table 37 Compounds 1081 to 1110 of formula I.E, wherein $X^1$, $X^2$ and $X^3$ are defined as in line P-5 of table P and the meaning of $R^1$ for each individual compound corresponds in each case to one line of table A.

Table 38 Compounds 1111 to 1140 of formula I.E, wherein $X^1$, $X^2$ and $X^3$ are defined as in line P-6 of table P and the meaning of $R^1$ for each individual compound corresponds in each case to one line of table A.

Table 39 Compounds 1141 to 1170 of formula I.E, wherein $X^1$, $X^2$ and $X^3$ are defined as in line P-7 of table P and the meaning of $R^1$ for each individual compound corresponds in each case to one line of table A.

Table 40 Compounds 1171 to 1200 of formula I.E, wherein $X^1$, $X^2$ and $X^3$ are defined as in line P-8 of table P and the meaning of $R^1$ for each individual compound corresponds in each case to one line of table A.

Table 41 Compounds 1201 to 1230 of formula I.F, wherein $X^1$, $X^2$ and $X^3$ are defined as in line P-1 of table P and the meaning of $R^1$ for each individual compound corresponds in each case to one line of table A.

Table 42 Compounds 1231 to 1260 of formula I.F, wherein $X^1$, $X^2$ and $X^3$ are defined as in line P-2 of table P and the meaning of $R^1$ for each individual compound corresponds in each case to one line of table A.

Table 43 Compounds 1261 to 1290 of formula I.F, wherein $X^1$, $X^2$ and $X^3$ are defined as in line P-3 of table P and the meaning of $R^1$ for each individual compound corresponds in each case to one line of table A.

Table 44 Compounds 1291 to 1320 of formula I.F, wherein $X^1$, $X^2$ and $X^3$ are defined as in line P-4 of table P and the meaning of $R^1$ for each individual compound corresponds in each case to one line of table A.

Table 45 Compounds 1321 to 1350 of formula I.F, wherein $X^1$, $X^2$ and $X^3$ are defined as in line P-5 of table P and the meaning of $R^1$ for each individual compound corresponds in each case to one line of table A.

Table 46 Compounds 1351 to 1380 of formula I.F, wherein $X^1$, $X^2$ and $X^3$ are defined as in line P-6 of table P and the meaning of $R^1$ for each individual compound corresponds in each case to one line of table A.

Table 47 Compounds 1381 to 1410 of formula I.F, wherein $X^1$, $X^2$ and $X^3$ are defined as in line P-7 of table P and the meaning of $R^1$ for each individual compound corresponds in each case to one line of table A.

Table 48 Compounds 1411 to 1440 of formula I.F, wherein $X^1$, $X^2$ and $X^3$ are defined as in line P-8 of table P and the meaning of $R^1$ for each individual compound corresponds in each case to one line of table A.

Table 49 Compounds 1441 to 1470 of formula I.G, wherein $X^1$, $X^2$ and $X^3$ are defined as in line P-1 of table P and the meaning of $R^1$ for each individual compound corresponds in each case to one line of table A.

Table 50 Compounds 1471 to 1500 of formula I.G, wherein $X^1$, $X^2$ and $X^3$ are defined as in line P-2 of table P and the meaning of $R^1$ for each individual compound corresponds in each case to one line of table A.

Table 51 Compounds 1501 to 1530 of formula I.G, wherein $X^1$, $X^2$ and $X^3$ are defined as in line P-3 of table P and the meaning of $R^1$ for each individual compound corresponds in each case to one line of table A.

Table 52 Compounds 1531 to 1560 of formula I.G, wherein $X^1$, $X^2$ and $X^3$ are defined as in line P-4 of table P and the meaning of $R^1$ for each individual compound corresponds in each case to one line of table A.

Table 53 Compounds 1561 to 1590 of formula I.G, wherein $X^1$, $X^2$ and $X^3$ are defined as in line P-5 of table P and the meaning of $R^1$ for each individual compound corresponds in each case to one line of table A.

Table 54 Compounds 1591 to 1620 of formula I.G, wherein $X^1$, $X^2$ and $X^3$ are defined as in line P-6 of table P and the meaning of $R^1$ for each individual compound corresponds in each case to one line of table A.

Table 55 Compounds 1621 to 1650 of formula I.G, wherein $X^1$, $X^2$ and $X^3$ are defined as in line P-7 of table P and the meaning of $R^1$ for each individual compound corresponds in each case to one line of table A.

Table 56 Compounds 1651 to 1680 of formula I.G, wherein $X^1$, $X^2$ and $X^3$ are defined as in line P-8 of table P and the meaning of $R^1$ for each individual compound corresponds in each case to one line of table A.

Table 57 Compounds 1681 to 1710 of formula I.H, wherein $X^1$, $X^2$ and $X^3$ are defined as in line P-1 of table P and the meaning of $R^1$ for each individual compound corresponds in each case to one line of table A.

Table 58 Compounds 1711 to 1740 of formula I.H, wherein $X^1$, $X^2$ and $X^3$ are defined as in line P-2 of table P and the meaning of $R^1$ for each individual compound corresponds in each case to one line of table A.

Table 59 Compounds 1741 to 1770 of formula I.H, wherein $X^1$, $X^2$ and $X^3$ are defined as in line P-3 of table P and the meaning of $R^1$ for each individual compound corresponds in each case to one line of table A.

Table 60 Compounds 1771 to 1800 of formula I.H, wherein $X^1$, $X^2$ and $X^3$ are defined as in line P-4 of table P and the meaning of $R^1$ for each individual compound corresponds in each case to one line of table A.

Table 61 Compounds 1801 to 1830 of formula I.H, wherein $X^1$, $X^2$ and $X^3$ are defined as in line P-5 of table P and the meaning of $R^1$ for each individual compound corresponds in each case to one line of table A.

Table 62 Compounds 1831 to 1860 of formula I.H, wherein $X^1$, $X^2$ and $X^3$ are defined as in line P-6 of table P and the meaning of $R^1$ for each individual compound corresponds in each case to one line of table A.

Table 63 Compounds 1861 to 1890 of formula I.H, wherein $X^1$, $X^2$ and $X^3$ are defined as in line P-7 of table P and the meaning of $R^1$ for each individual compound corresponds in each case to one line of table A.

Table 64 Compounds 1891 to 1920 of formula I.H, wherein $X^1$, $X^2$ and $X^3$ are defined as in line P-8 of table P and the meaning of $R^1$ for each individual compound corresponds in each case to one line of table A.

Table 65 Compounds 1921 to 1950 of formula I.J, wherein $X^1$, $X^2$ and $X^3$ are defined as in line P-1 of table P and the meaning of $R^1$ for each individual compound corresponds in each case to one line of table A.

Table 66 Compounds 1951 to 1980 of formula I.J, wherein $X^1$, $X^2$ and $X^3$ are defined as in line P-2 of table P and the meaning of $R^1$ for each individual compound corresponds in each case to one line of table A.

Table 67 Compounds 1981 to 2010 of formula I.J, wherein $X^1$, $X^2$ and $X^3$ are defined as in line P-3 of table P and the meaning of $R^1$ for each individual compound corresponds in each case to one line of table A.

Table 68 Compounds 2011 to 2040 of formula I.J, wherein $X^1$, $X^2$ and $X^3$ are defined as in line P-4 of table P and the meaning of $R^1$ for each individual compound corresponds in each case to one line of table A.

Table 69 Compounds 2041 to 2070 of formula I.J, wherein $X^1$, $X^2$ and $X^3$ are defined as in line P-5 of table P and the meaning of $R^1$ for each individual compound corresponds in each case to one line of table A.
Table 70 Compounds 2071 to 2100 of formula I.J, wherein $X^1$, $X^2$ and $X^3$ are defined as in line P-6 of table P and the meaning of $R^1$ for each individual compound corresponds in each case to one line of table A.
Table 71 Compounds 2101 to 2130 of formula I.J, wherein $X^1$, $X^2$ and $X^3$ are defined as in line P-7 of table P and the meaning of $R^1$ for each individual compound corresponds in each case to one line of table A.
Table 72 Compounds 2131 to 2160 of formula I.J, wherein $X^1$, $X^2$ and $X^3$ are defined as in line P-8 of table P and the meaning of $R^1$ for each individual compound corresponds in each case to one line of table A.
Table 73 Compounds 2161 to 2190 of formula I.K, wherein $X^1$, $X^2$ and $X^3$ are defined as in line P-1 of table P and the meaning of $R^1$ for each individual compound corresponds in each case to one line of table A.
Table 74 Compounds 2191 to 2220 of formula I.K, wherein $X^1$, $X^2$ and $X^3$ are defined as in line P-2 of table P and the meaning of $R^1$ for each individual compound corresponds in each case to one line of table A.
Table 75 Compounds 2221 to 2250 of formula I.K, wherein $X^1$, $X^2$ and $X^3$ are defined as in line P-3 of table P and the meaning of $R^1$ for each individual compound corresponds in each case to one line of table A.
Table 76 Compounds 2251 to 2280 of formula I.K, wherein $X^1$, $X^2$ and $X^3$ are defined as in line P-4 of table P and the meaning of $R^1$ for each individual compound corresponds in each case to one line of table A.
Table 77 Compounds 2281 to 2310 of formula I.K, wherein $X^1$, $X^2$ and $X^3$ are defined as in line P-5 of table P and the meaning of $R^1$ for each individual compound corresponds in each case to one line of table A.
Table 78 Compounds 2311 to 2340 of formula I.K, wherein $X^1$, $X^2$ and $X^3$ are defined as in line P-6 of table P and the meaning of $R^1$ for each individual compound corresponds in each case to one line of table A.
Table 79 Compounds 2341 to 2370 of formula I.K, wherein $X^1$, $X^2$ and $X^3$ are defined as in line P-7 of table P and the meaning of $R^1$ for each individual compound corresponds in each case to one line of table A.
Table 80 Compounds 2371 to 2400 of formula I.K, wherein $X^1$, $X^2$ and $X^3$ are defined as in line P-8 of table P and the meaning of $R^1$ for each individual compound corresponds in each case to one line of table A.
Table 81: Compounds 1a to 30a of formula I.A, wherein $X^1$, $X^2$ and $X^3$ are defined as in line P-1 of table P and the meaning of $R^1$ for each individual compound corresponds in each case to one line of table A-2.
Table 82: Compounds 31a to 60a of formula I.A, wherein $X^1$, $X^2$ and $X^3$ are defined as in line P-2 of table P and the meaning of $R^1$ for each individual compound corresponds in each case to one line of table A-2.
Table 83: Compounds 61a to 90a of formula I.A, wherein $X^1$, $X^2$ and $X^3$ are defined as in line P-3 of table P and the meaning of $R^1$ for each individual compound corresponds in each case to one line of table A-2.
Table 84: Compounds 91a to 120a of formula I.A, wherein $X^1$, $X^2$ and $X^3$ are defined as in line P-4 of table P and the meaning of $R^1$ for each individual compound corresponds in each case to one line of table A-2.
Table 85: Compounds 121a to 150a of formula I.A, wherein $X^1$, $X^2$ and $X^3$ are defined as in line P-5 of table P and the meaning of $R^1$ for each individual compound corresponds in each case to one line of table A-2.
Table 86: Compounds 151a to 180a of formula I.A, wherein $X^1$, $X^2$ and $X^3$ are defined as in line P-6 of table P and the meaning of $R^1$ for each individual compound corresponds in each case to one line of table A-2.
Table 87: Compounds 181a to 210a of formula I.A, wherein $X^1$, $X^2$ and $X^3$ are defined as in line P-7 of table P and the meaning of $R^1$ for each individual compound corresponds in each case to one line of table A-2.
Table 88: Compounds 211a to 240a of formula I.B, wherein $X^1$, $X^2$ and $X^3$ are defined as in line P-1 of table P and the meaning of $R^1$ for each individual compound corresponds in each case to one line of table A-2.
Table 89: Compounds 241a to 270a of formula I.B, wherein $X^1$, $X^2$ and $X^3$ are defined as in line P-2 of table P and the meaning of $R^1$ for each individual compound corresponds in each case to one line of table A-2.
Table 90: Compounds 271a to 300a of formula I.B, wherein $X^1$, $X^2$ and $X^3$ are defined as in line P-3 of table P and the meaning of $R^1$ for each individual compound corresponds in each case to one line of table A-2.
Table 91: Compounds 301a to 330a of formula I.B, wherein $X^1$, $X^2$ and $X^3$ are defined as in line P-4 of table P and the meaning of $R^1$ for each individual compound corresponds in each case to one line of table A-2.
Table 92: Compounds 331a to 360a of formula I.B, wherein $X^1$, $X^2$ and $X^3$ are defined as in line P-5 of table P and the meaning of $R^1$ for each individual compound corresponds in each case to one line of table A-2.
Table 93: Compounds 361a to 390a of formula I.B, wherein $X^1$, $X^2$ and $X^3$ are defined as in line P-6 of table P and the meaning of $R^1$ for each individual compound corresponds in each case to one line of table A-2.
Table 94: Compounds 391a to 420a of formula I.B, wherein $X^1$, $X^2$ and $X^3$ are defined as in line P-7 of table P and the meaning of $R^1$ for each individual compound corresponds in each case to one line of table A-2.
Table 95: Compounds 421a to 450a of formula I.C, wherein $X^1$, $X^2$ and $X^3$ are defined as in line P-1 of table P and the meaning of $R^1$ for each individual compound corresponds in each case to one line of table A-2.
Table 96: Compounds 451a to 480a of formula I.C, wherein $X^1$, $X^2$ and $X^3$ are defined as in line P-2 of table P and the meaning of $R^1$ for each individual compound corresponds in each case to one line of table A-2.
Table 97: Compounds 481a to 510a of formula I.C, wherein $X^1$, $X^2$ and $X^3$ are defined as in line P-3 of table P and the meaning of $R^1$ for each individual compound corresponds in each case to one line of table A-2.
Table 98: Compounds 511a to 540a of formula I.C, wherein $X^1$, $X^2$ and $X^3$ are defined as in line P-4 of table P and the meaning of $R^1$ for each individual compound corresponds in each case to one line of table A-2.
Table 99: Compounds 541a to 570a of formula I.C, wherein $X^1$, $X^2$ and $X^3$ are defined as in line P-5 of table P and the meaning of $R^1$ for each individual compound corresponds in each case to one line of table A-2.
Table 100: Compounds 571a to 600a of formula I.C, wherein $X^1$, $X^2$ and $X^3$ are defined as in line P-6 of table P and the meaning of $R^1$ for each individual compound corresponds in each case to one line of table A-2.
Table 101: Compounds 601a to 630a of formula I.C, wherein $X^1$, $X^2$ and $X^3$ are defined as in line P-7 of table P and the meaning of $R^1$ for each individual compound corresponds in each case to one line of table A-2.
Table 102: Compounds 631a to 660a of formula I.A, wherein $X^1$, $X^2$ and $X^3$ are defined as in line P-8 of table P and the meaning of $R^1$ for each individual compound corresponds in each case to one line of table A-2.

Table 103: Compounds 661a to 690a of formula I.B, wherein $X^1$, $X^2$ and $X^3$ are defined as in line P-8 of table P and the meaning of $R^1$ for each individual compound corresponds in each case to one line of table A-2.

Table 104: Compounds 691a to 720a of formula I.C, wherein $X^1$, $X^2$ and $X^3$ are defined as in line P-8 of table P and the meaning of $R^1$ for each individual compound corresponds in each case to one line of table A-2.

Table 105 Compounds 721a to 750a of formula I.D, wherein $X^1$, $X^2$ and $X^3$ are defined as in line P-1 of table P and the meaning of $R^1$ for each individual compound corresponds in each case to one line of table A-2.

Table 106 Compounds 751a to 780a of formula I.D, wherein $X^1$, $X^2$ and $X^3$ are defined as in line P-2 of table P and the meaning of $R^1$ for each individual compound corresponds in each case to one line of table A-2.

Table 107 Compounds 781a to 810a of formula I.D, wherein $X^1$, $X^2$ and $X^3$ are defined as in line P-3 of table P and the meaning of $R^1$ for each individual compound corresponds in each case to one line of table A-2.

Table 108 Compounds 811a to 840a of formula I.D, wherein $X^1$, $X^2$ and $X^3$ are defined as in line P-4 of table P and the meaning of $R^1$ for each individual compound corresponds in each case to one line of table A-2.

Table 109 Compounds 841a to 870a of formula I.D, wherein $X^1$, $X^2$ and $X^3$ are defined as in line P-5 of table P and the meaning of $R^1$ for each individual compound corresponds in each case to one line of table A-2.

Table 110 Compounds 871a to 900a of formula I.D, wherein $X^1$, $X^2$ and $X^3$ are defined as in line P-6 of table P and the meaning of $R^1$ for each individual compound corresponds in each case to one line of table A-2.

Table 111 Compounds 901a to 930a of formula I.D, wherein $X^1$, $X^2$ and $X^3$ are defined as in line P-7 of table P and the meaning of $R^1$ for each individual compound corresponds in each case to one line of table A-2.

Table 112 Compounds 931a to 960a of formula I.D, wherein $X^1$, $X^2$ and $X^3$ are defined as in line P-8 of table P and the meaning of $R^1$ for each individual compound corresponds in each case to one line of table A-2.

Table 113 Compounds 961a to 990a of formula I.E, wherein $X^1$, $X^2$ and $X^3$ are defined as in line P-1 of table P and the meaning of $R^1$ for each individual compound corresponds in each case to one line of table A-2.

Table 114 Compounds 991a to 1020a of formula I.E, wherein $X^1$, $X^2$ and $X^3$ are defined as in line P-2 of table P and the meaning of $R^1$ for each individual compound corresponds in each case to one line of table A-2.

Table 115 Compounds 1021a to 1050a of formula I.E, wherein $X^1$, $X^2$ and $X^3$ are defined as in line P-3 of table P and the meaning of $R^1$ for each individual compound corresponds in each case to one line of table A-2.

Table 116 Compounds 1051a to 1080a of formula I.E, wherein $X^1$, $X^2$ and $X^3$ are defined as in line P-4 of table P and the meaning of $R^1$ for each individual compound corresponds in each case to one line of table A-2.

Table 117 Compounds 1081a to 1110a of formula I.E, wherein $X^1$, $X^2$ and $X^3$ are defined as in line P-5 of table P and the meaning of $R^1$ for each individual compound corresponds in each case to one line of table A-2.

Table 118 Compounds 1111a to 1140a of formula I.E, wherein $X^1$, $X^2$ and $X^3$ are defined as in line P-6 of table P and the meaning of $R^1$ for each individual compound corresponds in each case to one line of table A-2.

Table 119 Compounds 1141a to 1170a of formula I.E, wherein $X^1$, $X^2$ and $X^3$ are defined as in line P-7 of table P and the meaning of $R^1$ for each individual compound corresponds in each case to one line of table A-2.

Table 120 Compounds 1171a to 1200a of formula I.E, wherein $X^1$, $X^2$ and $X^3$ are defined as in line P-8 of table P and the meaning of $R^1$ for each individual compound corresponds in each case to one line of table A-2.

Table 121 Compounds 1201a to 1230a of formula I.F, wherein $X^1$, $X^2$ and $X^3$ are defined as in line P-1 of table P and the meaning of $R^1$ for each individual compound corresponds in each case to one line of table A-2.

Table 122 Compounds 1231a to 1260a of formula I.F, wherein $X^1$, $X^2$ and $X^3$ are defined as in line P-2 of table P and the meaning of $R^1$ for each individual compound corresponds in each case to one line of table A-2.

Table 123 Compounds 1261a to 1290a of formula I.F, wherein $X^1$, $X^2$ and $X^3$ are defined as in line P-3 of table P and the meaning of $R^1$ for each individual compound corresponds in each case to one line of table A-2.

Table 124 Compounds 1291a to 1320a of formula I.F, wherein $X^1$, $X^2$ and $X^3$ are defined as in line P-4 of table P and the meaning of $R^1$ for each individual compound corresponds in each case to one line of table A-2.

Table 125 Compounds 1321a to 1350a of formula I.F, wherein $X^1$, $X^2$ and $X^3$ are defined as in line P-5 of table P and the meaning of $R^1$ for each individual compound corresponds in each case to one line of table A-2.

Table 126 Compounds 1351a to 1380a of formula I.F, wherein $X^1$, $X^2$ and $X^3$ are defined as in line P-6 of table P and the meaning of $R^1$ for each individual compound corresponds in each case to one line of table A-2.

Table 127 Compounds 1381a to 1410a of formula I.F, wherein $X^1$, $X^2$ and $X^3$ are defined as in line P-7 of table P and the meaning of $R^1$ for each individual compound corresponds in each case to one line of table A-2.

Table 128 Compounds 1411a to 1440a of formula I.F, wherein $X^1$, $X^2$ and $X^3$ are defined as in line P-8 of table P and the meaning of $R^1$ for each individual compound corresponds in each case to one line of table A-2.

Table 129 Compounds 1441a to 1470a of formula I.G, wherein $X^1$, $X^2$ and $X^3$ are defined as in line P-1 of table P and the meaning of $R^1$ for each individual compound corresponds in each case to one line of table A-2.

Table 130 Compounds 1471a to 1500a of formula I.G, wherein $X^1$, $X^2$ and $X^3$ are defined as in line P-2 of table P and the meaning of $R^1$ for each individual compound corresponds in each case to one line of table A-2.

Table 131 Compounds 1501a to 1530a of formula I.G, wherein $X^1$, $X^2$ and $X^3$ are defined as in line P-3 of table P and the meaning of $R^1$ for each individual compound corresponds in each case to one line of table A-2.

Table 132 Compounds 1531a to 1560a of formula I.G, wherein $X^1$, $X^2$ and $X^3$ are defined as in line P-4 of table P and the meaning of $R^1$ for each individual compound corresponds in each case to one line of table A-2.

Table 133 Compounds 1561a to 1590a of formula I.G, wherein $X^1$, $X^2$ and $X^3$ are defined as in line P-5 of table P and the meaning of $R^1$ for each individual compound corresponds in each case to one line of table A-2.

Table 134 Compounds 1591a to 1620a of formula I.G, wherein $X^1$, $X^2$ and $X^3$ are defined as in line P-6 of table P and the meaning of $R^1$ for each individual compound corresponds in each case to one line of table A-2.

Table 135 Compounds 1621a to 1650a of formula I.G, wherein $X^1$, $X^2$ and $X^3$ are defined as in line P-7 of table P and the meaning of $R^1$ for each individual compound corresponds in each case to one line of table A-2.
Table 136 Compounds 1651a to 1680a of formula I.G, wherein $X^1$, $X^2$ and $X^3$ are defined as in line P-8 of table P and the meaning of $R^1$ for each individual compound corresponds in each case to one line of table A-2.
Table 137 Compounds 1681a to 1710a of formula I.H, wherein $X^1$, $X^2$ and $X^3$ are defined as in line P-1 of table P and the meaning of $R^1$ for each individual compound corresponds in each case to one line of table A-2.
Table 138 Compounds 17111a to 1740a of formula I.H, wherein $X^1$, $X^2$ and $X^3$ are defined as in line P-2 of table P and the meaning of $R^1$ for each individual compound corresponds in each case to one line of table A-2.
Table 139 Compounds 1741a to 1770a of formula I.H, wherein $X^1$, $X^2$ and $X^3$ are defined as in line P-3 of table P and the meaning of $R^1$ for each individual compound corresponds in each case to one line of table A-2.
Table 140 Compounds 1771a to 1800a of formula I.H, wherein $X^1$, $X^2$ and $X^3$ are defined as in line P-4 of table P and the meaning of $R^1$ for each individual compound corresponds in each case to one line of table A-2.
Table 141 Compounds 1801a to 1830a of formula I.H, wherein $X^1$, $X^2$ and $X^3$ are defined as in line P-5 of table P and the meaning of $R^1$ for each individual compound corresponds in each case to one line of table A-2.
Table 142 Compounds 1831a to 1860a of formula I.H, wherein $X^1$, $X^2$ and $X^3$ are defined as in line P-6 of table P and the meaning of $R^1$ for each individual compound corresponds in each case to one line of table A-2.
Table 143 Compounds 1861a to 1890a of formula I.H, wherein $X^1$, $X^2$ and $X^3$ are defined as in line P-7 of table P and the meaning of $R^1$ for each individual compound corresponds in each case to one line of table A-2.
Table 144 Compounds 1891a to 1920a of formula I.H, wherein $X^1$, $X^2$ and $X^3$ are defined as in line P-8 of table P and the meaning of $R^1$ for each individual compound corresponds in each case to one line of table A-2.
Table 145 Compounds 1921a to 1950a of formula I.J, wherein $X^1$, $X^2$ and $X^3$ are defined as in line P-1 of table P and the meaning of $R^1$ for each individual compound corresponds in each case to one line of table A-2.
Table 146 Compounds 1951a to 1980a of formula I.J, wherein $X^1$, $X^2$ and $X^3$ are defined as in line P-2 of table P and the meaning of $R^1$ for each individual compound corresponds in each case to one line of table A-2.
Table 147 Compounds 1981a to 2010a of formula I.J, wherein $X^1$, $X^2$ and $X^3$ are defined as in line P-3 of table P and the meaning of $R^1$ for each individual compound corresponds in each case to one line of table A-2.
Table 148 Compounds 2011a to 2040a of formula I.J, wherein $X^1$, $X^2$ and $X^3$ are defined as in line P-4 of table P and the meaning of $R^1$ for each individual compound corresponds in each case to one line of table A-2.
Table 149 Compounds 2041a to 2070a of formula I.J, wherein $X^1$, $X^2$ and $X^3$ are defined as in line P-5 of table P and the meaning of $R^1$ for each individual compound corresponds in each case to one line of table A-2.
Table 150 Compounds 2071a to 2100a of formula I.J, wherein $X^1$, $X^2$ and $X^3$ are defined as in line P-6 of table P and the meaning of $R^1$ for each individual compound corresponds in each case to one line of table A-2.
Table 151 Compounds 2101a to 2130a of formula I.J, wherein $X^1$, $X^2$ and $X^3$ are defined as in line P-7 of table P and the meaning of $R^1$ for each individual compound corresponds in each case to one line of table A-2.
Table 152 Compounds 2131a to 2160a of formula I.J, wherein $X^1$, $X^2$ and $X^3$ are defined as in line P-8 of table P and the meaning of $R^1$ for each individual compound corresponds in each case to one line of table A-2.
Table 153 Compounds 2161a to 2190a of formula I.K, wherein $X^1$, $X^2$ and $X^3$ are defined as in line P-1 of table P and the meaning of $R^1$ for each individual compound corresponds in each case to one line of table A-2.
Table 154 Compounds 2191a to 2220a of formula I.K, wherein $X^1$, $X^2$ and $X^3$ are defined as in line P-2 of table P and the meaning of $R^1$ for each individual compound corresponds in each case to one line of table A-2.
Table 155 Compounds 2221a to 2250a of formula I.K, wherein $X^1$, $X^2$ and $X^3$ are defined as in line P-3 of table P and the meaning of $R^1$ for each individual compound corresponds in each case to one line of table A-2.
Table 156 Compounds 2251a to 2280a of formula I.K, wherein $X^1$, $X^2$ and $X^3$ are defined as in line P-4 of table P and the meaning of $R^1$ for each individual compound corresponds in each case to one line of table A-2.
Table 157 Compounds 2281a to 2310a of formula I.K, wherein $X^1$, $X^2$ and $X^3$ are defined as in line P-5 of table P and the meaning of $R^1$ for each individual compound corresponds in each case to one line of table A-2.
Table 158 Compounds 2311a to 2340a of formula I.K, wherein $X^1$, $X^2$ and $X^3$ are defined as in line P-6 of table P and the meaning of $R^1$ for each individual compound corresponds in each case to one line of table A-2.
Table 159 Compounds 2341a to 2370a of formula I.K, wherein $X^1$, $X^2$ and $X^3$ are defined as in line P-7 of table P and the meaning of $R^1$ for each individual compound corresponds in each case to one line of table A-2.
Table 160 Compounds 2371a to 2400a of formula I.K, wherein $X^1$, $X^2$ and $X^3$ are defined as in line P-8 of table P and the meaning of $R^1$ for each individual compound corresponds in each case to one line of table A-2.

TABLE A

| line | $R^1$ |
|---|---|
| A-1 | H |
| A-2 | $CH_3$ |
| A-3 | $CH_2CH_3$ |
| A-4 | $CH_2CH_2CH_3$ |
| A-5 | $CH(CH_3)_2$ |
| A-6 | $C_3H_5$ (cyclopropyl) |
| A-7 | $C_6H_5$ |
| A-8 | $CH_2$—$C_6H_5$ |
| A-9 | $CF_3$ |
| A-10 | $CHF_2$ |
| A-11 | $CH_2$—CN |
| A-12 | $CH_2CH_2$—CN |
| A-13 | C≡CH |
| A-14 | C≡CCH_3 |
| A-15 | $CH_2CH_2CH_2CH_3$ |
| A-16 | $C_3H_5$ |
| A-17 | $C_3H_5$ |
| A-18 | $CH_2$—$C_3H_5$ |
| A-19 | |
| A-20 | 4-F—$C_6H_4$ |
| A-21 | 4-Cl—$C_6H_4$ |
| A-22 | 2,4-$Cl_2$—$C_6H_3$ |
| A-23 | 2,4,6-$Cl_3$—$C_6H_2$ |
| A-24 | 2,4,6-$F_3$—$C_6H_2$ |
| A-25 | $CH_2$—$C_6H_5$ |
| A-26 | $CH_2$—(4-F—$C_6H_4$) |
| A-27 | $CH_2$—(4-Cl—$C_6H_4$) |
| A-28 | CH=CH—$C_6H_5$ |
| A-29 | CH=CH—(4-F—$C_6H_4$) |
| A-30 | CH=CH—(4-Cl—$C_6H_4$) |

TABLE A-2

| line | R¹ |
|---|---|
| A-31 | C(CH$_3$)$_3$ |
| A-32 | CH$_2$—CH=CH$_2$ |
| A-33 | CH$_2$—CH=CH—CH$_3$ |
| A-34 | CH$_2$—C(CH$_3$)=CH$_2$ |
| A-35 | CH=CHCH$_3$ |
| A-36 | C(CH$_3$)=CH$_2$ |
| A-37 | CH=CH$_2$ |
| A-38 | cyclohexyl |
| A-39 | cyclopentyl |
| A-40 | 4-OCH$_3$—C$_6$H$_4$ |
| A-41 | 4-CH$_3$—C$_6$H$_4$ |
| A-42 | 2,4-F$_2$—C$_6$H$_3$ |
| A-43 | CH$_2$—(4-CH$_3$)—C$_6$H$_4$ |
| A-44 | CH$_2$—(4-OCH$_3$)—C$_6$H$_4$ |
| A-45 | CH$_2$—(2,4-Cl$_2$)—C$_6$H$_3$ |
| A-46 | CH$_2$—(2,4-F$_2$)—C$_6$H$_3$ |
| A-47 | CH(CH$_3$)CH$_2$CH$_3$ |
| A-48 | CH$_2$—CH(CH$_3$)$_2$ |
| A-49 | CH$_2$—C≡C—CH$_3$ |
| A-50 | CH$_2$—C≡C—H |
| A-51 | CH$_2$—C≡C—CH$_2$CH$_3$ |
| A-52 | CH(CH$_3$)—C$_3$H$_5$ |
| A-53 | 1-(Cl)-cyclopropyl |
| A-54 | 1-(CH$_3$)-cyclopropyl |
| A-55 | 1-(CN)-cyclopropyl |
| A-56 | CH(CH$_3$)—CN |
| A-57 | CH$_2$—OCH$_3$ |
| A-58 | CH$_2$—OCH$_2$CH$_3$ |
| A-59 | CH(CH$_3$)—OCH$_3$ |
| A-60 | CH(CH$_3$)—OCH$_2$CH$_3$ |

The compounds I and the compositions according to the invention, respectively, are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and *Deuteromycetes* (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

The compounds I and the compositions according to the invention are particularly important in the control of a multitude of phytopathogenic fungi on various cultivated plants, such as cereals, e.g. wheat, rye, barley, triticale, oats or rice; beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called Stevia); natural rubber plants or ornamental and forestry plants, such as flowers, shrubs, broad-leaved trees or evergreens, e.g. conifers; and on the plant propagation material, such as seeds, and the crop material of these plants.

Preferably, compounds I and compositions thereof, respectively are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with compounds I and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://www.bio.org/speeches/pubs/er/agri_products.asp).

Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, such as auxin herbicides such as dicamba or 2,4-D; bleacher herbicides such as hydroxyl-phenylpyruvate dioxygenase (HPPD) inhibitors or phytoene desaturase (PDS) inhibittors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i.e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e.g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox, or ExpressSun® sunflowers (DuPont, USA) being tolerant to sulfonyl ureas, e.g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus Bacillus, particularly from Bacillus thuringiensis, such as δ-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. Photorhabdus spp. or Xenorhabdus spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of athropods, especially to beetles (Coleoptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the CryIF toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato cultivars, which express resistance genes acting against Phytophthora infestans derived from the mexican wild potato Solanum bulbocastanum) or T4-lysozym (e.g. potato cultivars capable of synthesizing these proteins with increased resistance against bacteria such as Erwinia amylvora). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

The compounds I and compositions thereof, respectively, are particularly suitable for controlling the following plant diseases:

Albugo spp. (white rust) on ornamentals, vegetables (e.g. A. candida) and sunflowers (e.g. A. tragopogonis); Alternaria spp. (Alternaria leaf spot) on vegetables, rape (A. brassicola or brassicae), sugar beets (A. tenuis), fruits, rice, soybeans, potatoes (e.g. A. solani or A. alternata), tomatoes (e.g. A. solani or A. alternata) and wheat; Aphanomyces spp. on sugar beets and vegetables; Ascochyta spp. on cereals and vegetables, e.g. A. tritici (anthracnose) on wheat and A. hordeion barley; Bipolaris and Drechslera spp. (teleomorph: Cochliobolus spp.), e.g. Southern leaf blight (D. maydis) or Northern leaf blight (B. zeicola) on corn, e.g. spot blotch (B. sorokiniana) on cereals and e.g. B. oryzae on rice and turfs; Blumeria (formerly Erysiphe) graminis (powdery mildew) on cereals (e.g. on wheat or barley); Botrytis cinerea (teleomorph: Botryotinia fuckeliana: grey mold) on fruits and berries (e.g. strawberries), vegetables (e.g. lettuce, carrots, celery and cabbages), rape, flowers, vines, forestry plants and wheat; Bremia lactucae (downy mildew) on lettuce; Ceratocystis (syn. Ophiostoma) spp. (rot or wilt) on broad-leaved trees and evergreens, e.g. C. ulmi (Dutch elm disease) on elms; Cercospora spp. (Cercospora leaf spots) on corn (e.g. Gray leaf spot: C. zeae-maydis), rice, sugar beets (e.g. C. beticola), sugar cane, vegetables, coffee, soybeans (e.g. C. sojina or C. kikuchii) and rice; Cladosporium spp. on tomatoes (e.g. *C. fulvum*: leaf mold) and cereals, e.g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e.g. *C. sativus*, anamorph: *B. sorokiniana*) and rice (e.g. *C. miyabeanus*, anamorph: *H. oryzae*); *Colletotrichum* (teleomorph: *Glomerella*) spp. (anthracnose) on cotton (e.g. *C. gossypii*), corn (e.g. *C. graminicola*: Anthracnose stalk rot), soft fruits, potatoes (e.g. *C. coccodes*: black dot), beans (e.g. *C. lindemuthianum*) and soybeans (e.g. *C. truncatum* or *C. gloeosporioides*); *Corticium* spp., e.g. *C. sasakii* (sheath blight) on rice; *Corynespora cassiicola* (leaf spots) on soybeans and ornamentals; *Cycloconium* spp., e.g. *C. oleaginum* on olive trees; *Cylindrocarpon* spp. (e.g. fruit tree canker or young vine decline, teleomorph: *Nectria* or *Neonectria* spp.) on fruit trees, vines (e.g. *C. liriodendri*, teleomorph: *Neonectria liriodendri* Black Foot Disease) and ornamentals; *Dematophora* (teleomorph: *Rosellinia*) necatrix (root and stem rot) on soybeans; *Diaporthe* spp., e.g. *D. phaseolorum* (damping off) on soybeans; *Drechslera* (syn. *Helminthosporium*, teleomorph: *Pyrenophora*) spp. on corn, cereals, such as barley (e.g. *D. teres*, net blotch) and wheat (e.g. *D. tritici-repentis*: tan spot), rice and turf; Esca (dieback, apoplexy) on vines, caused by *Formtiporia* (syn. *Phellinus*) *punctata, F. mediterranea, Phaeomoniella chlamydospora* (earlier *Phaeoacremonium chlamydosporum*), *Phaeoacremonium aleophilum* and/or *Botryosphaeria obtusa; Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e.g. *E. pisi*), such as cucurbits (e.g. *E. cichoracearum*), cabbages, rape (e.g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e.g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e.g. wheat or barley), *F. oxysporum* on tomatoes, *F. solanion* soybeans and *F. verticilloides* on corn; *Gaeumannomyces graminis* (take-all) on cereals (e.g. wheat or barley) and corn; *Gibberella* spp. on cereals (e.g. *G. zeae*) and rice (e.g. *G. fujikuroi* Bakanae disease); *Glomerella cingulata* on vines, pome fruits and other plants and *G. gossypii* on cotton; Grain-staining complex on rice; *Guignardia bidwellii* (black rot) on vines; *Gymnosporangium* spp. on rosaceous plants and junipers, e.g. *G. sabinae* (rust) on pears; *Helminthosporium* spp. (syn. *Drechslera*, teleomorph: *Cochliobolus*) on corn, cereals and rice; *Hemileia* spp., e.g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e.g. wheat or barley); *Microsphaera diffusa* (powdery mildew) on soybeans; *Monilinia* spp., e.g. *M. laxa, M. fructicola* and *M. fructigena* (bloom and twig blight, brown rot) on stone fruits and other rosaceous plants; *Mycosphaerella* spp. on cereals, bananas, soft fruits and ground nuts, such as e.g. *M. graminicola* (anamorph: *Septoria tritici, Septoria* blotch) on wheat or *M. fijiensis* (black Sigatoka disease) on bananas; *Peronospora* spp. (downy mildew) on cabbage (e.g. *P. brassicae*), rape (e.g. *P. parasitica*), onions (e.g. *P. destructor*), tobacco (*P. tabacina*) and soybeans (e.g. *P. manshurica*); *Phakopsora pachyrhizi* and *P. meibomiae* (soybean rust) on soybeans; *Phialophora* spp. on vines (e.g. *P. tracheiphila* and *P. tetraspora*) and soybeans (e.g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e.g. *P. viticola*: can and leaf spot) and soybeans (e.g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e.g. *P. capsici*), soybeans (e.g. *P. megasperma*, syn. *P. sojae*), potatoes and tomatoes (e.g. *P. infestans*: late blight) and broad-leaved trees (e.g. *P. ramorum*: sudden oak death); *Plasmodiophora brassicae* (club root) on cabbage, rape, radish and other plants; *Plasmopara* spp., e.g. *P. viticola* (grapevine downy mildew) on vines and *P. halstedii* on sunflowers; *Podosphaera* spp. (powdery mildew) on rosaceous plants, hop, pome and soft fruits, e.g. *P. leucotricha* on apples; *Polymyxa* spp., e.g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e.g. wheat or barley; *Pseudoperonospora* (downy mildew) on various plants, e.g. *P. cubensis* on cucurbits or *P. humili* on hop; *Pseudopezicula tracheiphila* (red fire disease or 'rotbrenner', anamorph: *Phialophora*) on vines; *Puccinia* spp. (rusts) on various plants, e.g. *P. triticina* (brown or leaf rust), *P. striiformis* (stripe or yellow rust), *P. hordei*(dwarf rust), *P. gramlinis* (stem or black rust) or *P. recondita* (brown or leaf rust) on cereals, such as e.g. wheat, barley or rye, *P. kuehnii* (orange rust) on sugar cane and *P. asparagion* asparagus; *Pyrenophora* (anamorph: *Drechslera*) *tritici-repentis* (tan spot) on wheat or *P. teres* (net blotch) on barley; *Pyricularia* spp., e.g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e.g. *P. ultimum* or *P. aphanidermatum*); *Ramularia* spp., e.g. *R. collo-cygni* (*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e.g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e.g. *S. scerotiorum*) and soybeans (e.g. *S. rolfsii* or *S. scerotiorum*); *Septoria* spp. on various plants, e.g. *S. glycines* (brown spot) on soybeans, *S. tritici* (*Septoria* blotch) on wheat and *S.* (syn. *Stagonospora*) *nodorum* (*Stagonospora* blotch) on cereals; *Uncinula* (syn. *Erysiphe*) *necator*(powdery mildew, anamorph: *Oidium tuckeri*) on vines; *Setospaeria* spp. (leaf blight) on corn (e.g. *S. turcicum*, syn. *Helminthosporium turcicum*) and turf; *Sphacelotheca* spp. (smut) on corn, (e.g. *S. reiliana*: head smut), sorghum und sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e.g. *S. nodorum* (*Stagonospora* blotch, teleomorph: *Leptosphaeria* [syn. *Phaeosphaeria] nodorum*) on wheat; *Synchytrium endobioticum* on potatoes (potato wart disease); *Taphrina* spp., e.g. *T. deformans* (leaf curl disease) on peaches and *T. pruni* (plum pocket) on plums; *Thielaviopsis* spp. (black root rot) on tobacco, pome fruits, vegetables, soybeans and cotton, e.g. *T. basicola* (syn. *Chalara elegans*); *Tilletia* spp. (common bunt or stinking smut) on cereals, such as e.g. *T. tritici* (syn. *T. caries*, wheat bunt) and *T. controversa*

(dwarf bunt) on wheat; *Typhula incarnata* (grey snow mold) on barley or wheat; *Urocystis* spp., e.g. *U. occulta* (stem smut) on rye; *Uromyces* spp. (rust) on vegetables, such as beans (e.g. *U. appendiculatus*, syn. *U. phaseoli*) and sugar beets (e.g. *U. betae*); *Ustilago* spp. (loose smut) on cereals (e.g. *U. nuda* and *U. avaenae*), corn (e.g. *U. maydis*: corn smut) and sugar cane; *Venturia* spp. (scab) on apples (e.g. *V. inaequalis*) and pears; and *Verticillium* spp. (wilt) on various plants, such as fruits and ornamentals, vines, soft fruits, vegetables and field crops, e.g. *V. dahliae* on strawberries, rape, potatoes and tomatoes.

The compounds I and compositions thereof, respectively, are also suitable for controlling harmful fungi in the protection of stored products or harvest and in the protection of materials. The term "protection of materials" is to be understood to denote the protection of technical and non-living materials, such as adhesives, glues, wood, paper and paperboard, textiles, leather, paint dispersions, plastics, coiling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans*, *Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichorma* spp., *Alternaria* spp., *Paecilomyces* spp. and Zygomycetes such as *Mucor* spp., and in addition in the protection of stored products and harvest the following yeast fungi are worthy of note: *Candida* spp. and *Saccharomyces cerevisae*.

The compounds I and compositions thereof, respectively, may be used for improving the health of a plant. The invention also relates to a method for improving plant health by treating a plant, its propagation material and/or the locus where the plant is growing or is to grow with an effective amount of compounds I and compositions thereof, respectively.

The term "plant health" is to be understood to denote a condition of the plant and/or its products which is determined by several indicators alone or in combination with each other such as yield (e.g. increased biomass and/or increased content of valuable ingredients), plant vigor (e.g. improved plant growth and/or greener leaves ("greening effect")), quality (e.g. improved content or composition of certain ingredients) and tolerance to abiotic and/or biotic stress. The above identified indicators for the health condition of a plant may be interdependent or may result from each other.

The compounds of formula I can be present in different crystal modifications whose biological activity may differ. They are likewise subject matter of the present invention.

The compounds I are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with compounds I as such or a composition comprising at least one compound I prophylactically either at or before planting or transplanting.

The invention also relates to agrochemical compositions comprising a solvent or solid carrier and at least one compound I and to the use for controlling harmful fungi.

An agrochemical composition comprises a fungicidally effective amount of a compound I. The term "effective amount" denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound I used.

The compounds I, their N-oxides and salts can be converted into customary types of agrochemical compositions, e.g. solutions, emulsions, suspensions, dusts, powders, pastes and granules. The composition type depends on the particular intended purpose; in each case, it should ensure a fine and uniform distribution of the compound according to the invention.

Examples for composition types are suspensions (SC, OD, FS), emulsifiable concentrates (EC), emulsions (EW, EO, ES), pastes, pastilles, wettable powders or dusts (WP, SP, SS, WS, DP, DS) or granules (GR, FG, GG, MG), which can be water-soluble or wettable, as well as gel formulations for the treatment of plant propagation materials such as seeds (GF).

Usually the composition types (e.g. SC, OD, FS, EC, WG, SG, WP, SP, SS, WS, GF) are employed diluted. Composition types such as DP, DS, GR, FG, GG and MG are usually used undiluted.

The compositions are prepared in a known manner (cf. U.S. Pat. No. 3,060,084, EP-A 707 445 (for liquid concentrates), Browning: "Agglomeration", Chemical Engineering, Dec. 4, 1967, 147-48, Perry's Chemical Engineer's Handbook, 4th Ed., McGraw-Hill, New York, 1963, S. 8-57 und ff. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman: Weed Control as a Science (J. Wiley & Sons, New York, 1961), Hance et al.: Weed Control Handbook (8th Ed., Blackwell Scientific, Oxford, 1989) and Mollet, H. and Grubemann, A.: Formulation technology (Wiley VCH Verlag, Weinheim, 2001).

The agrochemical compositions may also comprise auxiliaries which are customary in agrochemical compositions. The auxiliaries used depend on the particular application form and active substance, respectively.

Examples for suitable auxiliaries are solvents, solid carriers, dispersants or emulsifiers (such as further solubilizers, protective colloids, surfactants and adhesion agents), organic and anorganic thickeners, bactericides, anti-freezing agents, anti-foaming agents, if appropriate colorants and tackifiers or binders (e.g. for seed treatment formulations).

Suitable solvents are water, organic solvents such as mineral oil fractions of medium to high boiling point, such as kerosene or diesel oil, furthermore coal tar oils and oils of vegetable or animal origin, aliphatic, cyclic and aromatic hydrocarbons, e.g. toluene, xylene, paraffin, tetrahydronaphthalene, alkylated naphthalenes or their derivatives, alcohols such as methanol, ethanol, propanol, butanol and cyclohexanol, glycols, ketones such as cyclohexanone and gamma-butyrolactone, fatty acid dimethylamides, fatty acids and fatty acid esters and strongly polar solvents, e.g. amines such as N-methylpyrrolidone.

Solid carriers are mineral earths such as silicates, silica gels, talc, kaolins, limestone, lime, chalk, bole, loess, clays, dolomite, diatomaceous earth, calcium sulfate, magnesium sulfate, magnesium oxide, ground synthetic materials, fertilizers, such as, e.g., ammonium sulfate, ammonium phosphate, ammonium nitrate, ureas, and products of vegetable origin, such as cereal meal, tree bark meal, wood meal and nutshell meal, cellulose powders and other solid carriers.

Suitable surfactants (adjuvants, wtters, tackifiers, dispersants or emulsifiers) are alkali metal, alkaline earth metal and ammonium salts of aromatic sulfonic acids, such as lignin-soulfonic acid (Borresperse® types, Borregard, Norway) phenolsulfonic acid, naphthalenesulfonic acid (Morwet® types, Akzo Nobel, U.S.A.), dibutylnaphthalenesulfonic acid (Nekal® types, BASF, Germany), and fatty acids, alkylsulfonates, alkylarylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formaldehyde, polyoxy-ethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and proteins, denatured proteins, polysaccharides (e.g. methylcellulose), hydrophobically modified starches, polyvinyl alcohols (Mowiol® types, Clariant, Switzerland), polycarboxylates (Sokolan® types, BASF, Germany), polyalkoxylates, polyvinylamines (Lupasol® types, BASF, Germany), polyvinylpyrrolidone and the copolymers thereof.

Examples for thickeners (i.e. compounds that impart a modified flowability to compositions, i.e. high viscosity under static conditions and low viscosity during agitation) are polysaccharides and organic and anorganic clays such as Xanthan gum (Kelzan®, CP Kelco, U.S.A.), Rhodopol® 23 (Rhodia, France), Veegum® (R.T. Vanderbilt, U.S.A.) or Attaclay® (Engelhard Corp., NJ, USA).

Bactericides may be added for preservation and stabilization of the composition. Examples for suitable bactericides are those based on dichlorophene and benzyl-alcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie).

Examples for suitable anti-freezing agents are ethylene glycol, propylene glycol, urea and glycerin.

Examples for anti-foaming agents are silicone emulsions (such as e.g. Silikon® SRE, Wacker, Germany or Rhodorsil®, Rhodia, France), long chain alcohols, fatty acids, salts of fatty acids, fluoroorganic compounds and mixtures thereof.

Suitable colorants are pigments of low water solubility and water-soluble dyes. Examples to be mentioned und the designations rhodamin B, C. I. pigment red 112, C. I. solvent red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples for tackifiers or binders are polyvinylpyrrolidons, polyvinylacetates, polyvinyl alcohols and cellulose ethers (Tylose®, Shin-Etsu, Japan).

Powders, materials for spreading and dusts can be prepared by mixing or concomitantly grinding the compounds I and, if appropriate, further active substances, with at least one solid carrier.

Granules, e.g. coated granules, impregnated granules and homogeneous granules, can be prepared by binding the active substances to solid carriers. Examples of solid carriers are mineral earths such as silica gels, silicates, talc, kaolin, atta-clay, limestone, lime, chalk, bole, loess, clay, dolomite, diatomaceous earth, calcium sulfate, magnesium sulfate, magnesium oxide, ground synthetic materials, fertilizers, such as, e.g., ammonium sulfate, ammonium phosphate, ammonium nitrate, ureas, and products of vegetable origin, such as cereal meal, tree bark meal, wood meal and nutshell meal, cellulose powders and other solid carriers.

Examples for composition types are:

1. Composition Types for Dilution with Water i) Water-Soluble Concentrates (SL, LS)

10 parts by weight of a compound I according to the invention are dissolved in 90 parts by weight of water or in a water-soluble solvent. As an alternative, wetting agents or other auxiliaries are added. The active substance dissolves upon dilution with water. In this way, a composition having a content of 10% by weight of active substance is obtained.

ii) Dispersible Concentrates (DC)

20 parts by weight of a compound I according to the invention are dissolved in 70 parts by weight of cyclohexanone with addition of 10 parts by weight of a dispersant, e.g. polyvinylpyrrolidone. Dilution with water gives a dispersion. The active substance content is 20% by weight.

iii) Emulsifiable Concentrates (EC)

15 parts by weight of a compound I according to the invention are dissolved in 75 parts by weight of xylene with addition of calcium dodecylbenzenesulfonate and castor oil ethoxylate (in each case 5 parts by weight). Dilution with water gives an emulsion. The composition has an active substance content of 15% by weight.

iv) Emulsions (EW, EO, ES)

25 parts by weight of a compound I according to the invention are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (Ultraturrax) and made into a homogeneous emulsion. Dilution with water gives an emulsion. The composition has an active substance content of 25% by weight.

v) Suspensions (SC, OD, FS)

In an agitated ball mill, 20 parts by weight of a compound I according to the invention are comminuted with addition of 10 parts by weight of dispersants and wetting agents and 70 parts by weight of water or an organic solvent to give a fine active substance suspension. Dilution with water gives a stable suspension of the active substance. The active substance content in the composition is 20% by weight.

vi) Water-Dispersible Granules and Water-Soluble Granules (WG, SG)

50 parts by weight of a compound I according to the invention are ground finely with addition of 50 parts by weight of dispersants and wetting agents and prepared as water-dispersible or water-soluble granules by means of technical appliances (e.g. extrusion, spray tower, fluidized bed). Dilution with water gives a stable dispersion or solution of the active substance. The composition has an active substance content of 50% by weight.

vii) Water-Dispersible Powders and Water-Soluble Powders (WP, SP, SS, WS)

75 parts by weight of a compound I according to the invention are ground in a rotorstator mill with addition of 25 parts by weight of dispersants, wetting agents and silica gel. Dilution with water gives a stable dispersion or solution of the active substance. The active substance content of the composition is 75% by weight.

viii) Gel (GF)

In an agitated ball mill, 20 parts by weight of a compound I according to the invention are comminuted with addition of 10 parts by weight of dispersants, 1 part by weight of a gelling agent wetters and 70 parts by weight of water or of an organic solvent to give a fine suspension of the active substance. Dilution with water gives a stable suspension of the active substance, whereby a composition with 20% (w/w) of active substance is obtained.

2. Composition Types to be Applied Undiluted ix) Dustable Powders (DP, DS)

5 parts by weight of a compound I according to the invention are ground finely and mixed intimately with 95 parts by weight of finely divided kaolin. This gives a dustable composition having an active substance content of 5% by weight.

x) Granules (GR, FG, GG, MG)

0.5 parts by weight of a compound I according to the invention is ground finely and associated with 99.5 parts by weight of carriers. Current methods are extrusion, spray-drying or the fluidized bed. This gives granules to be applied undiluted having an active substance content of 0.5% by weight.

xi) ULV Solutions (UL)

10 parts by weight of a compound I according to the invention are dissolved in 90 parts by weight of an organic solvent, e.g. xylene. This gives a composition to be applied undiluted having an active substance content of 10% by weight.

The agrochemical compositions generally comprise between 0.01 and 95%, preferably between 0.1 and 90%, most preferably between 0.5 and 90%, by weight of active substance. The active substances are employed in a purity of from 90% to 100%, preferably from 95% to 100% (according to NMR spectrum).

Water-soluble concentrates (LS), flowable concentrates (FS), powders for dry treatment (DS), water-dispersible powders for slurry treatment (WS), water-soluble powders (SS), emulsions (ES) emulsifiable concentrates (EC) and gels (GF) are usually employed for the purposes of treatment of plant propagation materials, particularly seeds. These compositions can be applied to plant propagation materials, particularly seeds, diluted or undiluted. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying or treating agrochemical compounds and compositions thereof, respectively, on to plant propagation material, especially seeds, are known in the art, and include dressing, coating, pelleting, dusting, soaking and in-furrow application methods of the propagation material. In a preferred embodiment, the compounds or the compositions thereof, respectively, are applied on to the plant propagation material by a method such that germination is not induced, e.g. by seed dressing, pelleting, coating and dusting.

In a preferred embodiment, a suspension-type (FS) composition is used for seed treatment. Typically, a FS composition may comprise 1-800 g/l of active substance, 1-200 g/l Surfactant, 0 to 200 g/l antifreezing agent, 0 to 400 g/l of binder, 0 to 200 g/l of a pigment and up to 1 liter of a solvent, preferably water.

The active substances can be used as such or in the form of their compositions, e.g. in the form of directly sprayable solutions, powders, suspensions, dispersions, emulsions, oil dispersions, pastes, dustable products, materials for spreading, or granules, by means of spraying, atomizing, dusting, spreading, brushing, immersing or pouring. The application forms depend entirely on the intended purposes; it is intended to ensure in each case the finest possible distribution of the active substances according to the invention.

Aqueous application forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active substance concentrations in the ready-to-use preparations can be varied within relatively wide ranges. In general, they are from 0.0001 to 10%, preferably from 0.001 to 1% by weight of active substance.

The active substances may also be used successfully in the ultra-low-volume process (ULV), it being possible to apply compositions comprising over 95% by weight of active substance, or even to apply the active substance without additives.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required.

When used in the protection of materials or stored products, the amount of active substance applied depends on the kind of application area and on the desired effect. Amounts customarily applied in the protection of materials are, e.g., 0.001 g to 2 kg, preferably 0.005 g to 1 kg, of active substance per cubic meter of treated material.

Various types of oils, wetters, adjuvants, herbicides, bactericides, other fungicides and/or pesticides may be added to the active substances or the compositions comprising them, if appropriate not until immediately prior to use (tank mix). These agents can be admixed with the compositions according to the invention in a weight ratio of 1:100 to 100:1, preferably 1:10 to 10:1.

Adjuvants which can be used are in particular organic modified polysiloxanes such as Break Thru S 240®; alcohol alkoxylates such as Atplus 245®, Atplus MBA 1303®, Plurafac LF 300® and Lutensol ON 30®; EO/PO block polymers, e.g. Pluronic RPE 2035® and Genapol B®; alcohol ethoxylates such as Lutensol XP 80®; and dioctyl sulfosuccinate sodium such as Leophen RA®.

The compositions according to the invention can, in the use form as fungicides, also be present together with other active substances, e.g. with herbicides, insecticides, growth regulators, fungicides or else with fertilizers, as pre-mix or, if appropriate, not until immediately prior to use (tank mix).

Mixing the compounds I or the compositions comprising them in the use form as fungicides with other fungicides results in many cases in an expansion of the fungicidal spectrum of activity being obtained or in a prevention of fungicide resistance development. Furthermore, in many cases, synergistic effects are obtained.

The following list of active substances, in conjunction with which the compounds according to the invention can be used, is intended to illustrate the possible combinations but does not limit them:

A) Respiration inhibitors
  Inhibitors of complex III at $Q_o$ site (e.g. strobilurins): azoxystrobin, coumethoxystrobin, coumoxystrobin, dimoxystrobin, enestroburin, fenaminstrobin, fenoxystrobin/flufenoxystrobin, fluoxastrobin, kresoxim-methyl, metominostrobin, orysastrobin, picoxystrobin, pyraclostrobin, pyrametostrobin, pyraoxystrobin, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl)phenyl)-2-methoxyimino-N-methyl-acetamide, pyribencarb, triclopyricarb/chlorodincarb, famoxadone, fenamidone;
  inhibitors of complex III at Qi site: cyazofamid, amisulbrom,
  [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate; (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate;
  inhibitors of complex II (e.g. carboxamides): benodanil, bixafen, boscalid, carboxin, fenfuram, fluopyram, flutolanil, fluxapyroxad, furametpyr, isopyrazam, mepronil, oxylcarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, N-[9-(dichloromethylene)-1,2,3,4-tetrahydro-1,4-methanonaphthalen-5-yl]-3-(difluoromethyl)-1-methyl-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluorometh-yl)-1,5-dimethyl-N-(1,1,3-trimethylindan-4-yl)pyrazole-4-carboxamide, 3-(difluoro-methyl)-1,5-dimethyl-N-(1,1,3-trimethylindan-4-yl)pyrazole-4-carboxamide, 1,3,5-tri-methyl-N-(1,1,3-trimethylindan-4-yl)pyrazole-4-carboxamide;
  other respiration inhibitors (e.g. complex I, uncouplers): diflumetorim, (5,8-difluoroquinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organometal compounds: fentin salts, such as fentin-acetate, fentin chloride or fentin hydroxide; ametoctradin; and silthiofam;

B) Sterol biosynthesis inhibitors (SBI fungicides)
  C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole; -[re-(2S;3R)-3-(2-chlorophenyl)-2-(2,4-difluorophenyl)-oxiranylmethyl]-5-thiocyanato-1H-[1,2,4]triazole, 2-[rel-(2S;3-3-(2-chlorophenyl)-2-(2,4-difluorophenyl)-oxiranylmethyl]-2H-[1,2,4]triazole-3-thiol, imidazoles: imazalil, pefurazoate, prochloraz, triflumizol; pyrimidines, pyridines and piperazines: fenarimol, nuarimol, pyrifenox, triforine;
  Delta14-reductase inhibitors: aldimorph, dodemorph, dodemorph-acetate, fenpropimorph, tridemorph, fenpropidin, piperalin, spiroxamine;
  Inhibitors of 3-keto reductase: fenhexamid;

C) Nucleic acid synthesis inhibitors
  phenylamides or acyl amino acid fungicides: benalaxyl, benalaxyl-M, kiralaxyl, metalaxyl, metalaxyl-M (mefenoxam), ofurace, oxadixyl;
  others: hymexazole, octhilinone, oxolinic acid, bupirimate, 5-fluorocytosine, 5-fluoro-2-(p-tolylmethoxy)pyrimidin-4-amine, 5-fluoro-2-(4-fluorophenylmethoxy) pyrimidin-4-amine;

D) Inhibitors of cell division and cytoskeleton
  tubulin inhibitors, such as benzimidazoles, thiophanates: benomyl, carbendazim, fuberidazole, thiabendazole, thiophanate-methyl; triazolopyrimidines: 5-chloro-7-(4-methylpiperidin-1-yl)-6-(2,4,6-trifluorophenyl)-[1,2,4]triazolo[1,5-a]pyrimidine
  other cell division inhibitors: diethofencarb, ethaboxam, pencycuron, fluopicolide, zoxamide, metrafenone, pyriofenone;

E) Inhibitors of amino acid and protein synthesis
  methionine synthesis inhibitors (anilino-pyrimidines): cyprodinil, mepanipyrim, pyrimethanil;
  protein synthesis inhibitors: blasticidin-S, kasugamycin, kasugamycin hydrochloridehydrate, mildiomycin, streptomycin, oxytetracyclin, polyoxine, validamycin A;

F) Signal transduction inhibitors
  MAP/histidine kinase inhibitors: fluoroimid, iprodione, procymidone, vinclozolin, fenpiclonil, fludioxonil;
  G protein inhibitors: quinoxyfen;

G) Lipid and membrane synthesis inhibitors
  Phospholipid biosynthesis inhibitors: edifenphos, iprobenfos, pyrazophos, isoprothiolane;
  lipid peroxidation: dicloran, quintozene, tecnazene, tolclofos-methyl, biphenyl, chloroneb, etridiazole;
  phospholipid biosynthesis and cell wall deposition: dimethomorph, flumorph, mandipropamid, pyrimorph, benthiavalicarb, iprovalicarb, valifenalate and N-(1-(1-(4-cyano-phenyl)ethanesulfonyl)-but-2-yl)carbamic acid-(4-fluorophenyl)ester;
  compounds affecting cell membrane permeability and fatty acides: propamocarb, propamocarb-hydrochlorid
  fatty acid amide hydrolase inhibitors: 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone;

H) Inhibitors with Multi Site Action
  inorganic active substances: Bordeaux mixture, copper acetate, copper hydroxide, copper oxychloride, basic copper sulfate, sulfur;
  thio- and dithiocarbamates: ferbam, mancozeb, maneb, metam, metiram, propineb, thiram, zineb, ziram;

organochlorine compounds (e.g. phthalimides, sulfamides, chloronitriles): anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;

guanidines and others: guanidine, dodine, dodine free base, guazatine, guazatineacetate, iminoctadine, iminoctadine-triacetate, iminoctadine-tris(albesilate), dithianon; 2,6-dimethyl-1H,5H-[1,4]dithiino[2,3-c:5,6-c']dipyrrole-1,3,5,7(2H,6H)tetraone;

I) Cell wall synthesis inhibitors inhibitors of glucan synthesis: validamycin, polyoxin B; melanin synthesis inhibitors: pyroquilon, tricyclazole, carpropamid, dicyclomet, fenoxanil;

J) Plant defence inducers acibenzolar-5-methyl, probenazole, isotianil, tiadinil, prohexadione-calcium; phosphonates: fosetyl, fosetyl-aluminum, phosphorous acid and its salts;

K) Unknown mode of action bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxin-copper, proquinazid, tebufloquin, tecloftalam, triazoxide, 2-butoxy-6-iodo-3-propylchromen-4-one, N-(cyclopropyl-methoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl form amidine, N'-(5-difluoromethyl-2-methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, methoxy-acetic acid 6-tert-butyl-8-fluoro-2,3-dimethyl-quinolin-4-yl ester, N-Methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide, 3-[5-(4-methylphenyl)-2,3-dimethylisoxazolidin-3-yl]-pyridine, 3-[5-(4-chlorophenyl)-2,3-dimethyl-isoxazolidin-3-yl]-pyridine (pyrisoxazole), N-(6-methoxy-pyridin-3-yl)cyclopropanecarboxylic acid amide, 5-chloro-1-(4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide;

L) Antifungal biocontrol agents, plant bioactivators: *Ampelomyces quisqualis* (e.g. AQ 10® from Intrachem Bio GmbH & Co. KG, Germany), *Aspergillus flavus* (e.g. AFLA-GUARD® from Syngenta, CH), *Aureobasidium pullulans* (e.g. BOTECTOR® from bio-ferm GmbH, Germany), *Bacillus pumilus* (e.g. NRRL Accession No. B-30087 in SONATA® and BALLAD® Plus from AgraQuest Inc., USA), *Bacillus subtilis* (e.g. isolate NRRL-Nr. B-21661 in RHAPSODY®, SERENADE® MAX and SERENADE® ASO from AgraQuest Inc., USA), *Bacillus subtilis* var. *amyloliquefaciens* FZB24 (e.g. TAEGRO® from Novozyme Biologicals, Inc., USA), *Candida oleophila* I-82 (e.g. ASPIRE® from Ecogen Inc., USA), *Candida saitoana* (e.g. BIOCURE® (in mixture with lysozyme) and BIOCOAT® from Micro Flo Company, USA (BASF SE) and Arysta), Chitosan (e.g. ARMOUR-ZEN from BotriZen Ltd., NZ), *Clonostachys rosea* f. *catenulata*, also named *Gliocladium catenulatum* (e.g. isolate J1446: PRESTOP® from Verdera, Finland), *Coniothyrium minitans* (e.g. CONTANS® from Prophyta, Germany), *Cryphonectria parasitica* (e.g. *Endothia parasitica* from CNICM, France), *Cryptococcus albidus* (e.g. YIELD PLUS® from Anchor Bio-Technologies, South Africa), *Fusarium oxysporum* (e.g. BIOFOX® from S.I.B.P.A., Italy, FUSACLEAN® from Natural Plant Protection, France), *Metschnikowia fructicola* (e.g. SHEMER® from Agrogreen, Israel), *Microdochium dimerum* (e.g. ANTIBOT® from Agrauxine, France), *Phlebiopsis gigantea* (e.g. ROTSOP® from Verdera, Finland), *Pseudozyma flocculosa* (e.g. SPORODEX® from Plant Products Co. Ltd., Canada), *Pythium oligandrum* DV74 (e.g. POLYVERSUM® from Remeslo SSRO, Biopreparaty, Czech Rep.), *Reynoutria sachlinensis* (e.g. REGALIA® from Marrone BioInnovations, USA), *Talaromyces flavus* V117b (e.g. PROTUS® from Prophyta, Germany), *Trichoderma asperellum* SKT-1 (e.g. ECO-HOPE® from Kumiai Chemical Industry Co., Ltd., Japan), *T. atroviride* LC52 (e.g. SENTINEL® from Agrimm Technologies Ltd, NZ), *T. harzianum* T-22 (e.g. PLANTSHIELD® der Firma Bio-Works Inc., USA), *T. harzianum* TH 35 (e.g. ROOT PRO® from Mycontrol Ltd., Israel), *T. harzianum* T-39 (e.g. TRICHODEX® and TRICHODERMA 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ricerca, Italy), *T. polysporum* and *T. harzianum* (e.g. BINAB® from BINAB BioInnovation AB, Sweden), *T. stromaticum* (e.g. TRICOVAB® from C.E.P.L.A.C., Brazil), *T. virens* GL-21 (e.g. SOILGARD® from Certis LLC, USA), *T. viride* (e.g. TRIECO® from Ecosense Labs. (India) Pvt. Ltd., Indien, BIO-CURE® F from T. Stanes & Co. Ltd., Indien), *T. viride* TV1 (e.g. *T. viride* TV1 from Agribiotec srl, Italy), *Ulocladium oudemansii* HRU3 (e.g. BOTRY-ZEN® from Botry-Zen Ltd, NZ);

M) Growth regulators abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole;

N) Herbicides acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;

amino acid derivatives: bilanafos, glyphosate, glufosinate, sulfosate;

aryloxyphenoxypropionates: clodinafop, cyhalofop-butyl, fenoxaprop, fluazifop, haloxyfop, metamifop, propaquizafop, quizalofop, quizalofop-P-tefuryl;

Bipyridyls: diquat, paraquat;

(thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;

cyclohexanediones: butroxydim, clethodim, cycloxydim, profoxydim, sethoxydim, tepraloxydim, tralkoxydim;

dinitroanilines: benfluralin, ethalfluralin, oryzalin, pendimethalin, prodiamine, trifluralin;

diphenyl ethers: acifluorfen, aclonifen, bifenox, diclofop, ethoxyfen, fomesafen, lactofen, oxyfluorfen;

hydroxybenzonitriles: bomoxynil, dichlobenil, ioxynil;

imidazolinones: imazamethabenz, imazamox, imazapic, imazapyr, imazaquin, imazethapyr;

phenoxy acetic acids: clomeprop, 2,4-dichlorophenoxyacetic acid (2,4-D), 2,4-DB, dichlorprop, MCPA, MCPA-thioethyl, MCPB, Mecoprop;

pyrazines: chloridazon, flufenpyr-ethyl, fluthiacet, norflurazon, pyridate;

pyridines: aminopyralid, clopyralid, diflufenican, dithiopyr, fluridone, fluoroxypyr, picloram, picolinafen, thiazopyr;

sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxypyrimidin-2-yl)urea;

triazines: ametryn, atrazine, cyanazine, dimethametryn, ethiozin, hexazinone, metamitron, metribuzin, prometryn, simazine, terbuthylazine, terbutryn, triaziflam;

ureas: chlorotoluron, daimuron, diuron, fluometuron, isoproturon, linuron, methabenzthiazuron, tebuthiuron;

other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;

others: amicarbazone, aminotriazole, anilofos, beflubutamid, benazolin, bencarbazone, benfluresate, benzofenap, bentazone, benzobicyclon, bicyclopyrone, bromacil, bromobutide, butafenacil, butamifos, cafenstrole, carfentrazone, cinidon-ethyl, chlorthal, cinmethylin, clomazone, cumyluron, cyprosulfamide, dicamba, difenzoquat, diflufenzopyr, *Drechslera monoceras*, endothal, ethofumesate, etobenzanid, fenoxasulfone, fentrazamide, flumiclorac-pentyl, flumioxazin, flupoxam, fluorochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chlorophenyl)-5-fluoro-pyridine-2-carboxylic acid, 4-amino-3-chloro-6-(4-chloro-2-fluoro-3-methoxyphenyl)-pyridine-2-carboxylic acid methyl ester, and 4-amino-3-chloro-6-(4-chloro-3-dimethylamino-2-fluoro-phenyl)-pyridine-2-carboxylic acid methyl ester.

O) Insecticides organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

nicotinic receptor agonists/antagonists compounds: clothianidin, dinotefuran, flupyradifurone, imidacloprid, thiamethoxam, nitenpyram, acetamiprid, thiacloprid, 1-(2-chloro-thiazol-5-ylmethyl)-2-nitrimino-3,5-dimethyl-[1,3,5]triazinane;

GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;

macrocyclic lactone insecticides: abamectin, emamectin, milbemectin, lepimectin, spinosad, spinetoram;

mitochondrial electron transport inhibitor (METI) I acaricides: fenazaquin, pyridaben, tebufenpyrad, tolfenpyrad, flufenerim;

METI II and III compounds: acequinocyl, fluacyprim, hydramethylnon;

Uncouplers: chlorfenapyr;

oxidative phosphorylation inhibitors: cyhexatin, diafenthiuron, fenbutatin oxide, propargite;

moulting disruptor compounds: cryomazine;

mixed function oxidase inhibitors: piperonyl butoxide;

sodium channel blockers: indoxacarb, metaflumizone;

others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluoron, and pyrifluquinazon.

The present invention furthermore relates to agrochemical compositions comprising a mixture of at least one compound I (component 1) and at least one further active substance useful for plant protection, e.g. selected from the groups A) to O) (component 2), in particular one further fungicide, e.g. one or more fungicide from the groups A) to F), as described above, and if desired one suitable solvent or solid carrier. Those mixtures are of particular interest, since many of them at the same application rate show higher efficiencies against harmful fungi. Furthermore, combating harmful fungi with a mixture of compounds I and at least one fungicide from groups A) to L), as described above, is more efficient than combating those fungi with individual compounds I or individual fungicides from groups A) to L). By applying compounds I together with at least one active substance from groups A) to O) a synergistic effect can be obtained, i.e. more then simple addition of the individual effects is obtained (synergistic mixtures).

According to this invention, applying the compounds I together with at least one further active substance is to be understood to denote, that at least one compound of formula I and at least one further active substance occur simultaneously at the site of action (i.e. the harmful fungi to be controlled or their habitats such as infected plants, plant propagation materials, particularly seeds, surfaces, materials or the soil as well as plants, plant propagation materials, particularly seeds, soil, surfaces, materials or rooms to be protected from fungal attack) in a fungicidally effective amount. This can be obtained by applying the compounds I and at least one further active substance simultaneously, either jointly (e.g. as tank-mix) or separately, or in succession, wherein the time interval between the individual applications is selected to ensure that the active substance applied first still occurs at the site of action in a sufficient amount at the time of application of the further active substance(s). The order of application is not essential for working of the present invention.

In binary mixtures, i.e. compositions according to the invention comprising one compound I (component 1) and one further active substance (component 2), e.g. one active substance from groups A) to O), the weight ratio of component 1 and component 2 generally depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:3 to 3:1.

In ternary mixtures, i.e. compositions according to the invention comprising one compound I (component 1) and a first further active substance (component 2) and a second further active substance (component 3), e.g. two active substances from groups A) to O), the weight ratio of component 1 and component 2 depends from the properties of the active substances used, preferably it is in the range of from 1:50 to 50:1 and particularly in the range of from 1:10 to 10:1, and the weight ratio of component 1 and component 3 preferably is in the range of from 1:50 to 50:1 and particularly in the range of from 1:10 to 10:1.

The components can be used individually or already partially or completely mixed with one another to prepare the composition according to the invention. It is also possible for them to be packaged and used further as combination composition such as a kit of parts.

In one embodiment of the invention, the kits may include one or more, including all, components that may be used to prepare a subject agrochemical composition. E.g., kits may include one or more fungicide component(s) and/or an adjuvant component and/or a insecticide component and/or a growth regulator component and/or a herbicide. One or more of the components may already be combined together or preformulated. In those embodiments where more than two components are provided in a kit, the components may already be combined together and as such are packaged in a single container such as a vial, bottle, can, pouch, bag or canister. In other embodiments, two or more components of a kit may be packaged separately, i.e., not preformulated. As such, kits may include one or more separate containers such as vials, cans, bottles, pouches, bags or canisters, each container containing a separate component for an agrochemical composition. In both forms, a component of the kit may be applied separately from or together with the further components or as a component of a combination composition according to the invention for preparing the composition according to the invention.

The user applies the composition according to the invention usually from a predosage device, a knapsack sprayer, a spray tank or a spray plane. Here, the agrochemical composition is made up with water and/or buffer to the desired application concentration, it being possible, if appropriate, to add further auxiliaries, and the ready-to-use spray liquor or the agrochemical composition according to the invention is thus obtained. Usually, 50 to 500 liters of the ready-to-use spray liquor are applied per hectare of agricultural useful area, preferably 100 to 400 liters.

According to one embodiment, individual components of the composition according to the invention such as parts of a kit or parts of a binary or ternary mixture may be mixed by the user himself in a spray tank and further auxiliaries may be added, if appropriate (tank mix).

In a further embodiment, either individual components of the composition according to the invention or partially premixed components, e.g. components comprising compounds I and/or active substances from the groups A) to O), may be mixed by the user in a spray tank and further auxiliaries and additives may be added, if appropriate (tank mix).

In a further embodiment, either individual components of the composition according to the invention or partially premixed components, e.g. components comprising compounds I and/or active substances from the groups A) to O), can be applied jointly (e.g. after tankmix) or consecutively.

Preference is also given to mixtures comprising a compound I (component 1) and at least one active substance selected from group A) (component 2) and particularly selected from azoxystrobin, dimoxystrobin, fluoxastrobin, kresoxim-methyl, orysastrobin, picoxystrobin, pyraclostrobin, trifloxystrobin; famoxadone, fenamidone; bixafen, boscalid, fluopyram, fluxapyroxad, isopyrazam, penflufen, penthiopyrad, sedaxane; ametoctradin, cyazofamid, fluazinam, fentin salts, such as fentin acetate.

Preference is given to mixtures comprising a compound of formula I (component 1) and at least one active substance selected from group B) (component 2) and particularly selected from cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole, prochloraz, fenarimol, triforine; dodemorph, fenpropimorph, tridemorph, fenpropidin, spiroxamine; fenhexamid.

Preference is given to mixtures comprising a compound of formula I (component 1) and at least one active substance selected from group C) (component 2) and particularly selected from metalaxyl, (metalaxyl-M) mefenoxam, ofurace.

Preference is given to mixtures comprising a compound of formula I (component 1) and at least one active substance selected from group D) (component 2) and particularly selected from benomyl, carbendazim, thiophanate-methyl, ethaboxam, fluopicolide, zoxamide, metrafenone, pyriofenone.

Preference is also given to mixtures comprising a compound I (component 1) and at least one active substance selected from group E) (component 2) and particularly selected from cyprodinil, mepanipyrim, pyrimethanil.

Preference is also given to mixtures comprising a compound I (component 1) and at least one active substance selected from group F) (component 2) and particularly selected from iprodione, fludioxonil, vinclozolin, quinoxyfen.

Preference is also given to mixtures comprising a compound I (component 1) and at least one active substance selected from group G) (component 2) and particularly selected from dimethomorph, flumorph, iprovalicarb, benthiavalicarb, mandipropamid, propamocarb.

Preference is also given to mixtures comprising a compound I (component 1) and at least one active substance selected from group H) (component 2) and particularly selected from copper acetate, copper hydroxide, copper oxychloride, copper sulfate, sulfur, mancozeb, metiram, propineb, thiram, captafol, folpet, chlorothalonil, dichlofluanid, dithianon.

Preference is also given to mixtures comprising a compound I (component 1) and at least one active substance selected from group I) (component 2) and particularly selected from carpropamid and fenoxanil.

Preference is also given to mixtures comprising a compound I (component 1) and at least one active substance selected from group J) (component 2) and particularly selected from acibenzolar-S-methyl, probenazole, tiadinil, fosetyl, fosetyl-aluminium, $H_3PO_3$ and salts thereof.

Preference is also given to mixtures comprising a compound I (component 1) and at least one active substance selected from group K) (component 2) and particularly selected from cymoxanil, proquinazid and N-methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide.

Preference is also given to mixtures comprising a compound I (component 1) and at least one active substance selected from group L) (component 2) and particularly selected from *Bacillus subtilis* strain NRRL No. B-21661, *Bacillus pumilus* strain NRRL No. B-30087 and *Ulocladium oudemansii*.

Accordingly, the present invention furthermore relates to compositions comprising one compound I (component 1) and one further active substance (component 2), which further active substance is selected from the column "Component 2" of the lines B-1 to B-360 of Table B.

A further embodiment relates to the compositions B-1 to B-372 listed in Table B, where a row of Table B corresponds in each case to a fungicidal composition comprising one of the in the present specification individualized compounds of formula I (component 1) and the respective further active substance from groups A) to O) (component 2) stated in the row in question. Preferably, the compositions described comprise the active substances in synergistically effective amounts.

TABLE B

Composition comprising one indiviualized compound I and one further active substance from groups A) to O)

| Mixture | Component 1 | Component 2 |
|---|---|---|
| B-1 | one individualized compound I | Azoxystrobin |
| B-2 | one individualized compound I | Coumethoxystrobin |
| B-3 | one individualized compound I | Coumoxystrobin |
| B-4 | one individualized compound I | Dimoxystrobin |
| B-5 | one individualized compound I | Enestroburin |
| B-6 | one individualized compound I | Fenaminstrobin |
| B-7 | one individualized compound I | Fenoxystrobin/Flufenoxystrobin |
| B-8 | one individualized compound I | Fluoxastrobin |
| B-9 | one individualized compound I | Kresoxim-methyl |
| B-10 | one individualized compound I | Metominostrobin |
| B-11 | one individualized compound I | Orysastrobin |
| B-12 | one individualized compound I | Picoxystrobin |
| B-13 | one individualized compound I | Pyraclostrobin |
| B-14 | one individualized compound I | Pyrametostrobin |
| B-15 | one individualized compound I | Pyraoxystrobin |
| B-16 | one individualized compound I | Pyribencarb |
| B-17 | one individualized compound I | Trifloxystrobin |
| B-18 | one individualized compound I | Triclopyricarb/Chlorodincarb |
| B-19 | one individualized compound I | 2-[2-(2,5-dimethyl-phenoxymethyl)-phenyl]-3-methoxy-acrylic acid methyl ester |
| B-20 | one individualized compound I | 2-(2-(3-(2,6-dichlorophenyl)-1-methyl-allylideneaminooxymethyl)-phenyl)-2-methoxyimino-N-methyl-acetamide |
| B-21 | one individualized compound I | Benalaxyl |
| B-22 | one individualized compound I | Benalaxyl-M |
| B-23 | one individualized compound I | Benodanil |
| B-24 | one individualized compound I | Bixafen |
| B-25 | one individualized compound I | Boscalid |
| B-26 | one individualized compound I | Carboxin |
| B-27 | one individualized compound I | Fenfuram |
| B-28 | one individualized compound I | Fenhexamid |
| B-29 | one individualized compound I | Flutolanil |

TABLE B-continued

Composition comprising one indiviualized compound I
and one further active substance from groups A) to O)

| Mixture | Component 1 | Component 2 |
|---|---|---|
| B-30 | one individualized compound I | Fluxapyroxad |
| B-31 | one individualized compound I | Furametpyr |
| B-32 | one individualized compound I | Isopyrazam |
| B-33 | one individualized compound I | Isotianil |
| B-34 | one individualized compound I | Kiralaxyl |
| B-35 | one individualized compound I | Mepronil |
| B-36 | one individualized compound I | Metalaxyl |
| B-37 | one individualized compound I | Metalaxyl-M |
| B-38 | one individualized compound I | Ofurace |
| B-39 | one individualized compound I | Oxadixyl |
| B-40 | one individualized compound I | Oxycarboxin |
| B-41 | one individualized compound I | Penflufen |
| B-42 | one individualized compound I | Penthiopyrad |
| B-43 | one individualized compound I | Sedaxane |
| B-44 | one individualized compound I | Tecloftalam |
| B-45 | one individualized compound I | Thifluzamide |
| B-46 | one individualized compound I | Tiadinil |
| B-47 | one individualized compound I | 2-Amino-4-methyl-thiazole-5-carboxylic acid anilide |
| B-48 | one individualized compound I | N-(4'-trifluoromethylthiobiphenyl-2-yl)-3-difluoromethyl-1-methyl-1H-pyrazole-4-carboxamide |
| B-49 | one individualized compound I | N-(2-(1,3,3-trimethyl-butyl)-phenyl)-1,3-dimethyl-5-fluoro-1H-pyrazole-4-carboxamide |
| B-50 | one individualized compound I | N-[9-(dichloromethylene)-1,2,3,4-tetrahydro-1,4-methanonaphthalen-5-yl]-3-(difluoromethyl)-1-methyl-1H-pyrazole-4-carboxamide |
| B-51 | one individualized compound I | Dimethomorph |
| B-52 | one individualized compound I | Flumorph |
| B-53 | one individualized compound I | Pyrimorph |
| B-54 | one individualized compound I | Flumetover |
| B-55 | one individualized compound I | Fluopicolide |
| B-56 | one individualized compound I | Fluopyram |
| B-57 | one individualized compound I | Zoxamide |
| B-58 | one individualized compound I | Carpropamid |
| B-59 | one individualized compound I | Diclocymet |
| B-60 | one individualized compound I | Mandipropamid |
| B-61 | one individualized compound I | Oxytetracyclin |
| B-62 | one individualized compound I | Silthiofam |
| B-63 | one individualized compound I | N-(6-methoxy-pyridin-3-yl) cyclopropanecarboxylic acid amide |
| B-64 | one individualized compound I | Azaconazole |
| B-65 | one individualized compound I | Bitertanol |
| B-66 | one individualized compound I | Bromuconazole |
| B-67 | one individualized compound I | Cyproconazole |
| B-68 | one individualized compound I | Difenoconazole |
| B-69 | one individualized compound I | Diniconazole |
| B-70 | one individualized compound I | Diniconazole-M |
| B-71 | one individualized compound I | Epoxiconazole |
| B-72 | one individualized compound I | Fenbuconazole |
| B-73 | one individualized compound I | Fluquinconazole |
| B-74 | one individualized compound I | Flusilazole |
| B-75 | one individualized compound I | Flutriafol |
| B-76 | one individualized compound I | Hexaconazol |
| B-77 | one individualized compound I | Imibenconazole |
| B-78 | one individualized compound I | Ipconazole |
| B-79 | one individualized compound I | Metconazole |
| B-80 | one individualized compound I | Myclobutanil |
| B-81 | one individualized compound I | Oxpoconazol |
| B-82 | one individualized compound I | Paclobutrazol |
| B-83 | one individualized compound I | Penconazole |
| B-84 | one individualized compound I | Propiconazole |
| B-85 | one individualized compound I | Prothioconazole |
| B-86 | one individualized compound I | Simeconazole |
| B-87 | one individualized compound I | Tebuconazole |
| B-88 | one individualized compound I | Tetraconazole |
| B-89 | one individualized compound I | Triadimefon |
| B-90 | one individualized compound I | Triadimenol |
| B-91 | one individualized compound I | Triticonazole |
| B-92 | one individualized compound I | Uniconazole |
| B-93 | one individualized compound I | Cyazofamid |
| B-94 | one individualized compound I | Imazalil |
| B-95 | one individualized compound I | Imazalil-sulfate |

TABLE B-continued

Composition comprising one indiviualized compound I and one further active substance from groups A) to O)

| Mixture | Component 1 | Component 2 |
| --- | --- | --- |
| B-96 | one individualized compound I | Pefurazoate |
| B-97 | one individualized compound I | Prochloraz |
| B-98 | one individualized compound I | Triflumizole |
| B-99 | one individualized compound I | Benomyl |
| B-100 | one individualized compound I | Carbendazim |
| B-101 | one individualized compound I | Fuberidazole |
| B-102 | one individualized compound I | Thiabendazole |
| B-103 | one individualized compound I | Ethaboxam |
| B-104 | one individualized compound I | Etridiazole |
| B-105 | one individualized compound I | Hymexazole |
| B-106 | one individualized compound I | 2-(4-Chloro-phenyl)-N-[4-(3,4-dimethoxy-phenyl)-isoxazol-5-yl]-2-prop-2-yn-yloxy-acetamide |
| B-107 | one individualized compound I | Fluazinam |
| B-108 | one individualized compound I | Pyrifenox |
| B-109 | one individualized compound I | 3-[5-(4-Chloro-phenyl)-2,3-dimethyl-isoxazolidin-3-yl]-pyridine (Pyrisoxazole) |
| B-110 | one individualized compound I | 3-[5-(4-Methyl-phenyl)-2,3-dimethyl-isoxazolidin-3-yl]-pyridine |
| B-111 | one individualized compound I | Bupirimate |
| B-112 | one individualized compound I | Cyprodinil |
| B-113 | one individualized compound I | 5-Fluorocytosine |
| B-114 | one individualized compound I | 5-Fluoro-2-(p-tolylmethoxy)pyrimidin-4-amine |
| B-115 | one individualized compound I | 5-Fluoro-2-(4-fluorophenylmethoxy)-pyrimidin-4-amine |
| B-116 | one individualized compound I | Diflumetorim |
| B-117 | one individualized compound I | (5,8-Difluoroquinazolin-4-yl)-{2-[2-fluoro-4-(4-trifluoromethylpyridin-2-yloxy)-phenyl]-ethyl}-amine |
| B-118 | one individualized compound I | Fenarimol |
| B-119 | one individualized compound I | Ferimzone |
| B-120 | one individualized compound I | Mepanipyrim |
| B-121 | one individualized compound I | Nitrapyrin |
| B-122 | one individualized compound I | Nuarimol |
| B-123 | one individualized compound I | Pyrimethanil |
| B-124 | one individualized compound I | Triforine |
| B-125 | one individualized compound I | Fenpiclonil |
| B-126 | one individualized compound I | Fludioxonil |
| B-127 | one individualized compound I | Aldimorph |
| B-128 | one individualized compound I | Dodemorph |
| B-129 | one individualized compound I | Dodemorph-acetate |
| B-130 | one individualized compound I | Fenpropimorph |
| B-131 | one individualized compound I | Tridemorph |
| B-132 | one individualized compound I | Fenpropidin |
| B-133 | one individualized compound I | Fluoroimid |
| B-134 | one individualized compound I | Iprodione |
| B-135 | one individualized compound I | Procymidone |
| B-136 | one individualized compound I | Vinclozolin |
| B-137 | one individualized compound I | Famoxadone |
| B-138 | one individualized compound I | Fenamidone |
| B-139 | one individualized compound I | Flutianil |
| B-140 | one individualized compound I | Octhilinone |
| B-141 | one individualized compound I | Probenazole |
| B-142 | one individualized compound I | Fenpyrazamine |
| B-143 | one individualized compound I | Acibenzolar-S-methyl |
| B-144 | one individualized compound I | Ametoctradin |
| B-145 | one individualized compound I | Amisulbrom |
| B-146 | one individualized compound I | [(3S,6S,7R,8R)-8-benzyl-3-[(3-isobutyryloxymethoxy-4-methoxypyridine-2-carbonyl)amino]-6-methyl-4,9-dioxo-[1,5]dioxonan-7-yl] 2-methylpropanoate |
| B-147 | one individualized compound I | [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate |
| B-148 | one individualized compound I | [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl] 2-methylpropanoate |
| B-149 | one individualized compound I | [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl] 2-methylpropanoate |

TABLE B-continued

Composition comprising one indiviualized compound I
and one further active substance from groups A) to O)

| Mixture | Component 1 | Component 2 |
| --- | --- | --- |
| B-150 | one individualized compound I | [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methyl-propanoate |
| B-151 | one individualized compound I | Anilazin |
| B-152 | one individualized compound I | Blasticidin-S |
| B-153 | one individualized compound I | Captafol |
| B-154 | one individualized compound I | Captan |
| B-155 | one individualized compound I | Chinomethionat |
| B-156 | one individualized compound I | Dazomet |
| B-157 | one individualized compound I | Debacarb |
| B-158 | one individualized compound I | Diclomezine |
| B-159 | one individualized compound I | Difenzoquat, |
| B-160 | one individualized compound I | Difenzoquat-methylsulfate |
| B-161 | one individualized compound I | Fenoxanil |
| B-162 | one individualized compound I | Folpet |
| B-163 | one individualized compound I | Oxolinsäure |
| B-164 | one individualized compound I | Piperalin |
| B-165 | one individualized compound I | Proquinazid |
| B-166 | one individualized compound I | Pyroquilon |
| B-167 | one individualized compound I | Quinoxyfen |
| B-168 | one individualized compound I | Triazoxid |
| B-169 | one individualized compound I | Tricyclazole |
| B-170 | one individualized compound I | 2-Butoxy-6-iodo-3-propyl-chromen-4-one |
| B-171 | one individualized compound I | 5-Chloro-1-(4,6-dimethoxy-pyrimidin-2-yl)-2-methyl-1H-benzoimidazole |
| B-172 | one individualized compound I | 5-Chloro-7-(4-methyl-piperidin-1-yl)-6-(2,4,6-trifluoro-phenyl)-[1,2,4]triazolo[1,5-a]pyrimidine |
| B-173 | one individualized compound I | Ferbam |
| B-174 | one individualized compound I | Mancozeb |
| B-175 | one individualized compound I | Maneb |
| B-176 | one individualized compound I | Metam |
| B-177 | one individualized compound I | Methasulphocarb |
| B-178 | one individualized compound I | Metiram |
| B-179 | one individualized compound I | Propineb |
| B-180 | one individualized compound I | Thiram |
| B-181 | one individualized compound I | Zineb |
| B-182 | one individualized compound I | Ziram |
| B-183 | one individualized compound I | Diethofencarb |
| B-184 | one individualized compound I | Benthiavalicarb |
| B-185 | one individualized compound I | Iprovalicarb |
| B-186 | one individualized compound I | Propamocarb |
| B-187 | one individualized compound I | Propamocarb hydrochlorid |
| B-188 | one individualized compound I | Valifenalate |
| B-189 | one individualized compound I | N-(1-(1-(4-cyanophenyl)ethanesulfonyl)-but-2-yl) carbamic acid-(4-fluoro-phenyl) ester |
| B-190 | one individualized compound I | Dodine |
| B-191 | one individualized compound I | Dodine free base |
| B-192 | one individualized compound I | Guazatine |
| B-193 | one individualized compound I | Guazatine-acetate |
| B-194 | one individualized compound I | Iminoctadine |
| B-195 | one individualized compound I | Iminoctadine-triacetate |
| B-196 | one individualized compound I | Iminoctadine-tris(albesilate) |
| B-197 | one individualized compound I | Kasugamycin |
| B-198 | one individualized compound I | Kasugamycin-hydrochloride-hydrate |
| B-199 | one individualized compound I | Polyoxine |
| B-200 | one individualized compound I | Streptomycin |
| B-201 | one individualized compound I | Validamycin A |
| B-202 | one individualized compound I | Binapacryl |
| B-203 | one individualized compound I | Dicloran |
| B-204 | one individualized compound I | Dinobuton |
| B-205 | one individualized compound I | Dinocap |
| B-206 | one individualized compound I | Nitrothal-isopropyl |
| B-207 | one individualized compound I | Tecnazen |
| B-208 | one individualized compound I | Fentin salts |
| B-209 | one individualized compound I | Dithianon |
| B-210 | one individualized compound I | Isoprothiolane |
| B-211 | one individualized compound I | Edifenphos |
| B-212 | one individualized compound I | Fosetyl, Fosetyl-aluminium |
| B-213 | one individualized compound I | Iprobenfos |
| B-214 | one individualized compound I | Phosphorous acid ($H_3PO_3$) and derivatives |

TABLE B-continued

Composition comprising one indiviualized compound I and one further active substance from groups A) to O)

| Mixture | Component 1 | Component 2 |
|---|---|---|
| B-215 | one individualized compound I | Pyrazophos |
| B-216 | one individualized compound I | Tolclofos-methyl |
| B-217 | one individualized compound I | Chlorothalonil |
| B-218 | one individualized compound I | Dichlofluanid |
| B-219 | one individualized compound I | Dichlorophen |
| B-220 | one individualized compound I | Flusulfamide |
| B-221 | one individualized compound I | Hexachlorbenzene |
| B-222 | one individualized compound I | Pencycuron |
| B-223 | one individualized compound I | Pentachlorophenol and salts |
| B-224 | one individualized compound I | Phthalide |
| B-225 | one individualized compound I | Quintozene |
| B-226 | one individualized compound I | Thiophanate Methyl |
| B-227 | one individualized compound I | Tolylfluanid |
| B-228 | one individualized compound I | N-(4-chloro-2-nitro-phenyl)-N-ethyl-4-methyl-benzenesulfonamide |
| B-229 | one individualized compound I | Bordeaux mixture |
| B-230 | one individualized compound I | Copper acetate |
| B-231 | one individualized compound I | Copper hydroxide |
| B-232 | one individualized compound I | Copper oxychloride |
| B-233 | one individualized compound I | basic Copper sulfate |
| B-234 | one individualized compound I | Sulfur |
| B-235 | one individualized compound I | Biphenyl |
| B-236 | one individualized compound I | Bronopol |
| B-237 | one individualized compound I | Cyflufenamid |
| B-238 | one individualized compound I | Cymoxanil |
| B-239 | one individualized compound I | Diphenylamin |
| B-240 | one individualized compound I | Metrafenone |
| B-241 | one individualized compound I | Pyriofenone |
| B-242 | one individualized compound I | Mildiomycin |
| B-243 | one individualized compound I | Oxin-copper |
| B-244 | one individualized compound I | Prohexadione calcium |
| B-245 | one individualized compound I | Spiroxamine |
| B-246 | one individualized compound I | Tebufloquin |
| B-247 | one individualized compound I | Tolylfluanid |
| B-248 | one individualized compound I | N-(Cyclopropylmethoxyimino-(6-difluoromethoxy-2,3-difluoro-phenyl)-methyl)-2-phenyl acetamide |
| B-249 | one individualized compound I | N'-(4-(4-chloro-3-trifluoromethyl-phenoxy)-2,5-dimethyl-phenyl)-N-ethyl-N-methyl formamidine |
| B-250 | one individualized compound I | N'-(4-(4-fluoro-3-trifluoromethyl-phenoxy)-2,5-dimethyl-phenyl)-N-ethyl-N-methyl formamidine |
| B-251 | one individualized compound I | N'-(2-methyl-5-trifluoromethyl-4-(3-trimethylsilanyl-propoxy)-phenyl)-N-ethyl-N-methyl formamidine |
| B-252 | one individualized compound I | N'-(5-difluoromethyl-2-methyl-4-(3-trimethylsilanyl-propoxy)-phenyl)-N-ethyl-N-methyl formamidine |
| B-253 | one individualized compound I | 2-{1-[2-(5-Methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide |
| B-254 | one individualized compound I | 2-{1-[2-(5-Methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide |
| B-255 | one individualized compound I | 1-[4-[4-[5-(2,6-difluorophenyl)-4,5-dihydro-3-isoxazolyl]-2-thiazolyl]-1-piperidinyl]-2-[5-methyl-3-(trifluoro-methyl)-1H-pyrazol-1-yl]ethanone |
| B-256 | one individualized compound I | Methoxy-acetic acid 6-tert-butyl-8-fluoro-2,3-dimethyl-quinolin-4-yl ester |
| B-257 | one individualized compound I | N-Methyl-2-{1-[(5-methyl-3-trifluoro-methyl-1H-pyrazol-1-yl)-acetyl]-piperidin-4-yl}-N-[(1R)-1,2,3,4-tetrahydro-naphthalen-1-yl]-4-thiazolecarboxamide |
| B-258 | one individualized compound I | *Bacillus subtilis* NRRL No. B-21661 |
| B-259 | one individualized compound I | *Bacillus pumilus* NRRL No. B-30087 |
| B-260 | one individualized compound I | *Ulocladium oudemansii* |
| B-261 | one individualized compound I | Carbaryl |
| B-262 | one individualized compound I | Carbofuran |
| B-263 | one individualized compound I | Carbosulfan |

TABLE B-continued

Composition comprising one indiviualized compound I and one further active substance from groups A) to O)

| Mixture | Component 1 | Component 2 |
|---|---|---|
| B-264 | one individualized compound I | Methomylthiodicarb |
| B-265 | one individualized compound I | Bifenthrin |
| B-266 | one individualized compound I | Cyfluthrin |
| B-267 | one individualized compound I | Cypermethrin |
| B-268 | one individualized compound I | alpha-Cypermethrin |
| B-269 | one individualized compound I | zeta-Cypermethrin |
| B-270 | one individualized compound I | Deltamethrin |
| B-271 | one individualized compound I | Esfenvalerate |
| B-272 | one individualized compound I | Lambda-cyhalothrin |
| B-273 | one individualized compound I | Permethrin |
| B-274 | one individualized compound I | Tefluthrin |
| B-275 | one individualized compound I | Diflubenzuron |
| B-276 | one individualized compound I | Flufenoxuron |
| B-277 | one individualized compound I | Lufenuron |
| B-278 | one individualized compound I | Teflubenzuron |
| B-279 | one individualized compound I | Spirotetramate |
| B-280 | one individualized compound I | Clothianidin |
| B-281 | one individualized compound I | Dinotefuran |
| B-282 | one individualized compound I | Imidacloprid |
| B-283 | one individualized compound I | Thiamethoxam |
| B-284 | one individualized compound I | Acetamiprid |
| B-285 | one individualized compound I | Thiacloprid |
| B-286 | one individualized compound I | Endosulfan |
| B-287 | one individualized compound I | Fipronil |
| B-288 | one individualized compound I | Abamectin |
| B-289 | one individualized compound I | Emamectin |
| B-290 | one individualized compound I | Spinosad |
| B-291 | one individualized compound I | Spinetoram |
| B-292 | one individualized compound I | Hydramethylnon |
| B-293 | one individualized compound I | Chlorfenapyr |
| B-294 | one individualized compound I | Fenbutatin oxide |
| B-295 | one individualized compound I | Indoxacarb |
| B-296 | one individualized compound I | Metaflumizone |
| B-297 | one individualized compound I | Flonicamid |
| B-298 | one individualized compound I | Lubendiamide |
| B-299 | one individualized compound I | Chlorantraniliprole |
| B-300 | one individualized compound I | Cyazypyr (HGW86) |
| B-301 | one individualized compound I | Cyflumetofen |
| B-302 | one individualized compound I | Acetochlor |
| B-303 | one individualized compound I | Dimethenamid |
| B-304 | one individualized compound I | metolachlor |
| B-305 | one individualized compound I | Metazachlor |
| B-306 | one individualized compound I | Glyphosate |
| B-307 | one individualized compound I | Glufosinate |
| B-308 | one individualized compound I | Sulfosate |
| B-309 | one individualized compound I | Clodinafop |
| B-310 | one individualized compound I | Fenoxaprop |
| B-311 | one individualized compound I | Fluazifop |
| B-312 | one individualized compound I | Haloxyfop |
| B-313 | one individualized compound I | Paraquat |
| B-314 | one individualized compound I | Phenmedipham |
| B-315 | one individualized compound I | Clethodim |
| B-316 | one individualized compound I | Cycloxydim |
| B-317 | one individualized compound I | Profoxydim |
| B-318 | one individualized compound I | Sethoxydim |
| B-319 | one individualized compound I | Tepraloxydim |
| B-320 | one individualized compound I | Pendimethalin |
| B-321 | one individualized compound I | Prodiamine |
| B-322 | one individualized compound I | Trifluralin |
| B-323 | one individualized compound I | Acifluorfen |
| B-324 | one individualized compound I | Bromoxynil |
| B-325 | one individualized compound I | Imazamethabenz |
| B-326 | one individualized compound I | Imazamox |
| B-327 | one individualized compound I | Imazapic |
| B-328 | one individualized compound I | Imazapyr |
| B-329 | one individualized compound I | Imazaquin |
| B-330 | one individualized compound I | Imazethapyr |
| B-331 | one individualized compound I | 2,4-Dichlorophenoxyacetic acid (2,4-D) |
| B-332 | one individualized compound I | Chloridazon |
| B-333 | one individualized compound I | Clopyralid |
| B-334 | one individualized compound I | Fluroxypyr |
| B-335 | one individualized compound I | Picloram |
| B-336 | one individualized compound I | Picolinafen |
| B-337 | one individualized compound I | Bensulfuron |
| B-338 | one individualized compound I | Chlorimuron-ethyl |

TABLE B-continued

Composition comprising one indiviualized compound I and one further active substance from groups A) to O)

| Mixture | Component 1 | Component 2 |
|---|---|---|
| B-339 | one individualized compound I | Cyclosulfamuron |
| B-340 | one individualized compound I | Iodosulfuron |
| B-341 | one individualized compound I | Mesosulfuron |
| B-342 | one individualized compound I | Metsulfuron-methyl |
| B-343 | one individualized compound I | Nicosulfuron |
| B-344 | one individualized compound I | Rimsulfuron |
| B-345 | one individualized compound I | Triflusulfuron |
| B-346 | one individualized compound I | Atrazine |
| B-347 | one individualized compound I | Hexazinone |
| B-348 | one individualized compound I | Diuron |
| B-349 | one individualized compound I | Florasulam |
| B-350 | one individualized compound I | Pyroxasulfone |
| B-351 | one individualized compound I | Bentazone |
| B-352 | one individualized compound I | Cinidon-ethyl |
| B-353 | one individualized compound I | Cinmethylin |
| B-354 | one individualized compound I | Dicamba |
| B-355 | one individualized compound I | Diflufenzopyr |
| B-356 | one individualized compound I | Quinclorac |
| B-357 | one individualized compound I | Quinmerac |
| B-358 | one individualized compound I | Mesotrione |
| B-359 | one individualized compound I | Saflufenacil |
| B-360 | one individualized compound I | Topramezone |
| B-361 | one individualized compound I | 3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate |
| B-362 | one individualized compound I | [rel-(2S; 3R)-3-(2-chlorophenyl)-2-(2,4-difluorophenyl)-oxiranylmethyl]-5-thiocyanato-1H-[1,2,4]triazole, |
| B-363 | one individualized compound I | 2-[rel-(2S; 3R)-3-(2-chlorophenyl)-2-(2,4-difluorophenyl)-oxiranylmethyl]-2H-[1,2,4]triazole-3-thiol |
| B-364 | one individualized compound I | 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone |
| B-365 | one individualized compound I | 2,6-dimethyl-1H,5H-[1,4]dithiino[2,3-c:5,6-c']dipyrrole-1,3,5,7(2H,6H)-tetraone |
| B-366 | one individualized compound I | flupyradifurone |
| B-367 | one individualized compound I | 3-(difluoromethyl)-1-methyl-N-(1,1,3-trimethylindan-4-yl)pyrazole-4-carboxamide |
| B-368 | one individualized compound I | 3-(trifluoromethyl)-1-methyl-N-(1,1,3-trimethylindan-4-yl)pyrazole-4-carboxamide |
| B-369 | one individualized compound I | 1,3-dimethyl-N-(1,1,3-trimethylindan-4-yl)pyrazole-4-carboxamide |
| B-370 | one individualized compound I | 3-(trifluoromethyl)-1,5-dimethyl-N-(1,1,3-trimethylindan-4-yl)pyrazole-4-carboxamide |
| B-371 | one individualized compound I | 3-(difluoromethyl)-1,5-dimethyl-N-(1,1,3-trimethylindan-4-yl)pyrazole-4-carboxamide |
| B-372 | one individualized compound I | 1,3,5-trimethyl-N-(1,1,3-trimethylindan-4-yl)pyrazole-4-carboxamide |

The active substances referred to as component 2, their preparation and their activity against harmful fungi is known (cf.: http://www.alanwood.net/pesticides/); these substances are commercially available. The compounds described by IUPAC nomenclature, their preparation and their fungicidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. No. 3,296,272; U.S. Pat. No. 3,325, 503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028,657).

The mixtures of active substances can be prepared as compositions comprising besides the active ingredients at least one inert ingredient by usual means, e.g. by the means given for the compositions of compounds I.

Concerning usual ingredients of such compositions reference is made to the explanations given for the compositions containing compounds I.

The mixtures of active substances according to the present invention are suitable as fungicides, as are the compounds of formula I. They are distinguished by an outstanding effectiveness against a broad spectrum of phytopathogenic fungi, especially from the classes of the Ascomycetes, Basidiomycetes, *Deuteromycetes* and Peronosporomycetes (syn. Oomycetes). In addition, it is referred to the explanations regarding the fungicidal activity of the compounds and the compositions containing compounds I, respectively.

I. SYNTHESIS EXAMPLES

With due modification of the starting compounds, the procedures shown in the synthesis examples below were used to obtain further compounds I. The resulting compounds, together with physical data, are listed in Table I below.

Example 1

Compound I-5

Step 1

1-[2-chloro-4-(2,4-difluorophenoxy)phenyl]ethanone

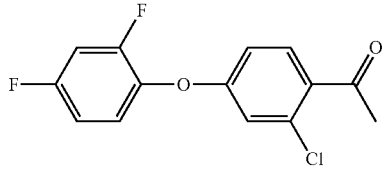 [SMILES: CC(=O)c1ccc(Oc2ccc(F)cc2F)cc1Cl]

A solution of 50 g of 4-Fluoro-2-Chloro-acetophenone was dissolved in NMP (250 mL). $K_2CO_3$ (52.1 g) and 2,4-difluorophenol (41.5 g) was added and the reaction mixture was heated to 120° C. for 16 h. MTBE (500 mL) was added and the organic phase was extract 3 times with sat-aq. $NH_4Cl$— solution. The organic phase was separated and the aqueous phase was three times extracted with MTBE (300 mL). The combined organic layers were washed with sat $NaHCO_3$-solution, sat aq. NaCl and dried over $Na_2SO_4$. 1-[2-chloro-4-(2,4-difluorophenoxy)phenyl]ethanone (100 g) was obtained as a brown oil and used in the next step without further purification (HPLC-MS, Rt=1.23 min, masse=283).

Step 2

2-[2-chloro-4-(2,4-difluorophenoxy)phenyl]-2-methyl-oxirane

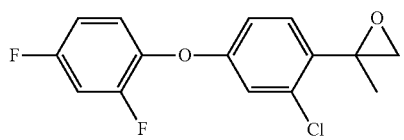 [SMILES: CC1(c2ccc(Oc3ccc(F)cc3F)cc2Cl)CO1]

NaH (4.39 g) was suspended in THF/DMSO (400 mL) and $Me_3S$—I (35.4 g) was added carefully in small portions. 30 min after completed addition, a solution of 1-[2-chloro-4-(2, 4-difluorophenoxy)phenyl]ethanone (25 g) in 50 mL THF was added. After stirring overnight, the reaction mixture was diluted with MTBE and sat aq. $NH_4Cl$-Sol was added. The organic phase was separated and the aqueous phase was three times extracted with MTBE (300 mL). the combined organic layers were washed with sat $NaHCO_3$-solution, sat aq. NaCl and dried over $Na_2SO_4$. 2-[2-chloro-4-(2,4-difluorophenoxy)phenyl]-2-methyl-oxirane (23.5 g) was obtained as a brown oil and used in the next step without further purification.
$^1$H-NMR ($CDCl_3$; 400 MHz) (ppm)=1.65 (s, 3H); 2.8-3.0 (dd, 2H); 6.75-7.1 (m, 5H); 7.4 (d, 1H).

Step 3

2-[2-chloro-4-(2,4-difluorophenoxy)phenyl]-1-(1,2,4-triazol-1-yl)propan-2-ol

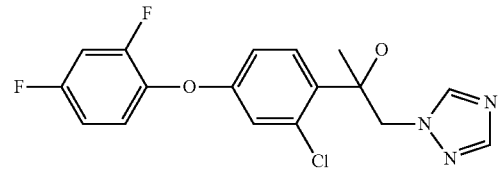 [SMILES: CC(O)(Cn1cncn1)c1ccc(Oc2ccc(F)cc2F)cc1Cl]

2-[2-chloro-4-(2,4-difluorophenoxy)phenyl]-2-methyl-oxirane (5.0 g), triazole (5.24 g) and NaOH (1.52 g) were dissolved in NMP (50 mL) and the reaction mixture heated to 120° C. and stirred for 15 h. The reaction mixture was diluted with MTBE (200 mL) and extracted three times with 100 mL $H_2O$. The organic phase was washed with sat. aq. NaCl-sol and dried over $Na_2SO_4$. After evaporation and column chromatography ($CH_2Cl_2$/MeOH, O-20% MeOH), 2-[2-chloro-4-(2,4-difluorophenoxy)phenyl]-1-(1,2,4-triazol-1-yl)propan-2-ol (2.7 g) was obtained as an orange oil.

Example 2

Compound I-2

1-[2-[2-chloro-4-(2,4-dichlorophenoxy)phenyl]-2-methoxy-propyl]-1,2,4-triazole

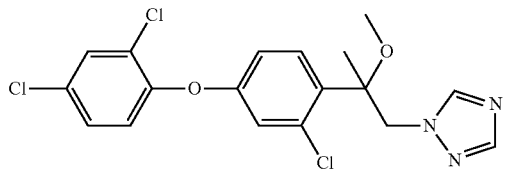 [SMILES: COC(C)(Cn1cncn1)c1ccc(Oc2ccc(Cl)cc2Cl)cc1Cl]

2-[2-chloro-4-(2,4-dichlorophenoxy)phenyl]-1-(1,2,4-triazol-1-yl)propan-2-ol was synthesized in an analogous manner as 2-[2-chloro-4-(2,4-difluorophenoxy)phenyl]-1-(1,2,4-triazol-1-yl)propan-2-ol.

The tertiary alcohol 2-[2-chloro-4-(2,4-dichlorophenoxy)phenyl]-1-(1,2,4-triazol-1-yl)propan-2-ol (370 mg) was dissolved in THf (15 mL) and NaH (28 mg) was added in one portion. After 30 min, methyl Iodide (158 mg) was added and heated to reflux for 14 h. sat. aq. NaCl (10 mL) was added and after separation of the phases the aqueous phase was extracted three times with $CH_2Cl_2$. The combined organic phases were washed with brine and dried over $Na_2SO_4$. Flash chromatography yielded the target compound as colorless oil (195 mg).

The compounds I listed in Table I have been prepared in an analogous manner.

TABLE I

| ex.-no. | $R^1$ | $R^2$ | $X^1$ | $X^2$ | $X^3$ | HPLC * $R_t$ (min) |
|---|---|---|---|---|---|---|
| I-1 | $CH_3$ | H | Cl | Cl | H | 1.19 |
| I-2 | $CH_3$ | $CH_3$ | Cl | Cl | H | 1.28 |
| I-3 | H | H | Cl | Cl | H | 1.12 |
| I-4 | H | $CH_3$ | Cl | Cl | H | 1.26 |
| I-5 | $CH_3$ | H | F | F | H | 1.05 |

* (conditions B): HPLC methods Data for Table I:
Mobile Phase: A: Water + 0.1% TFA, B: acetonitrile; Gradient: 5% B to 100% B in 1.5 min; Temperature: 60° C.; MS method: ESI positive; mass area (m/z): 10-700; Flow: 0.8 ml/min to 1.0 ml/min in 1.5 min; Column: Kinetex XB C18 1.7μ 50 × 2.1 mm; Apparatus: Shimadzu Nexera LC-30 LCMS-2020

II. EXAMPLES OF THE ACTION AGAINST HARMFUL FUNGI

The fungicidal action of the compounds of the formula I was demonstrated by the following experiments:
Green House
The spray solutions were prepared in several steps:
The stock solution were prepared: a mixture of acetone and/or dimethylsulfoxide and the wetting agent/emulsifier Wettol, which is based on ethoxylated alkylphenoles, in a relation (volume) solvent-emulsifier of 99 to 1 was added to 25 mg of the compound to give a total of 5 ml. Water was then added to total volume of 100 ml. This stock solution was diluted with the described solvent-emulsifier-water mixture to the given concentration.

1. Protective control of soy bean rust on soy beans caused by *Phakopsora pachyrhizi* (Phakpa P1)

Leaves of pot-grown soy bean seedlings were sprayed to run-off with an aqueous suspension, containing the concentration of active ingredient or their mixture as described below. The plants were allowed to air-dry. The trial plants were cultivated for 1 day in a greenhouse chamber at 23-27° C. and a relative humidity between 60 and 80%.Then the plants were inoculated with spores of *Phakopsora pachyrhizi*. To ensure the success the artificial inoculation, the plants were transferred to a humid chamber with a relative humidity of about 95% and 20 to 24 C for 24 h. The trial plants were cultivated for fourteen days in a greenhouse chamber at 23-27° C. and a relative humidity between 60 and 80%. The extent of fungal attack on the leaves was visually assessed as % diseased leaf area. In this test, the plants which had been treated with 300 ppm of the active substance from example I-1, showed an infection of 10% whereas the untreated plants were 90% infected.

2. Preventative fungicidal control of *Botrytis cinerea*on leaves of green pepper (Botrci P1)

Young seedlings of green pepper were grown in pots to the 4 to 5 leaf stage. These plants were sprayed to run-off with an aqueous suspension, containing the concentration of active ingredient or their mixture mentioned in the table below. The next day the plants were inoculated with a aqueous biomalt solution containing the spore suspension of *Botrytis cinerea*. Then the plants were immediately transferred to a humid chamber. After 5 days at 22 to 24° C. and a relative humidity close to 100% the extent of fungal attack on the leaves was visually assessed as % diseased leaf area. In this test, the plants which had been treated with 300 ppm of the active substance from examples I-1, I-2 and I-3, respectively, showed an infection of 5% or less whereas the untreated plants were 100% infected.

3. Preventative control of brown rust on wheat caused by *Puccinia recondita* (Puccrt P1)

The first two developed leaves of pot-grown wheat seedling were sprayed to run-off with an aqueous suspension, containing the concentration of active ingredient or their mixture as described below. The next day the plants were inoculated with spores of *Puccinia recondita*. To ensure the success the artificial inoculation, the plants were transferred to a humid chamber without light and a relative humidity of 95 to 99% and 20 to 24° C. for 24 h. Then the trial plants were cultivated for 6 days in a greenhouse chamber at 20-24° C. and a relative humidity between 65 and 70%. The extent of fungal attack on the leaves was visually assessed as % diseased leaf area. In this test, the plants which had been treated with 300 ppm of the active substance from examples I-1, I-2 and I-4, respectively, showed an infection of 15% or less whereas the untreated plants were 80% infected.

4. Preventative fungicidal control of early blight on tomatoes (*Alternaria solani*) (Alteso P1)

Young seedlings of tomato plants were grown in pots. These plants were sprayed to run-off with an aqueous suspension, containing the concentration of active ingredient or mixture mentioned in the table below. The next day, the treated plants were inoculated with an aqueous suspension of *Alternaria solani*. Then the trial plants were immediately transferred to a humid chamber. After 5 days at 18 to 20° C. and a relative humidity close to 100%, the extent of fungal attack on the leaves was visually assessed as % diseased leaf area. In this test, the plants which had been treated with 300 ppm of the active substance from examples I-1, I-2, I-3 and I-4, respectively, showed an infection of 20% or less whereas the untreated plants were 90% infected.

The invention claimed is:
1. A compound of formula I

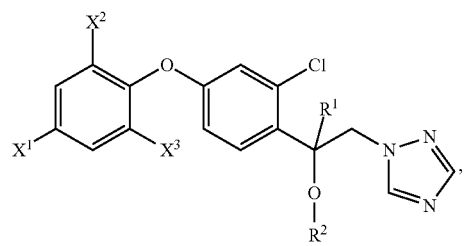

wherein:
$X^1, X^2$ independently of each other are selected from halogen;
$X^3$ is hydrogen or halogen;
$R^1$ is $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_6$-alkyl, phenyl, phenyl-$C_1$-$C_4$-alkyl, phenyl-$C_2$-$C_4$-alkenyl or phenyl-$C_2$-$C_4$-alkynyl,
$R^2$ is hydrogen, $C_1$-$C_6$-alkyl, $C_2$-$C_6$-alkenyl, $C_2$-$C_6$-alkynyl, $C_3$-$C_8$-cycloalkyl, cycloalkyl-$C_1$-$C_6$-alkyl, phenyl, phenyl-$C_1$-$C_4$-alkyl, phenyl-C7-$C_4$-alkenyl or phenyl-$C_1$-$C_4$-alkenyl,
wherein the aliphatic groups $R^1$ and/or $R^2$ may carry 1, 2, 3 or up to the maximum possible number of identical or different groups $R^a$ which independently of one another are selected from the group consisting of halogen, CN, nitro, $C_1$-$C_4$-alkoxy and $C_1$-$C_4$-halogenalkoxy;

wherein the cycloalkyl and/or phenyl moieties of $R^1$ and/or $R^2$ may carry 1, 2, 3, 4, 5 or up to the maximum number of identical or different groups $R^b$ which independently of one another are selected from the group consisting of halogen, CN, nitro, $C_1$-$C_4$-alkyl, $C_1$-$C_4$-alkoxy, $C_1$-$C_4$-halogenalkyl and $C_1$-$C_4$-halogenalkoxy;

or an N-oxide and an agriculturally acceptable salt thereof.

2. The compound according to claim 1, wherein $X^1$ and $X^2$ are independently of each other selected from F and Cl.

3. The compound according to claim 1, wherein $X^3$ is hydrogen, F or Cl.

4. The compound according to claim 1, wherein $R^1$ is hydrogen, $C_1$-$C_4$-alkyl, allyl, $C_2$-$C_6$-alkynyl, cyclopropyl, cyclopropylmethyl, phenyl, benzyl, phenylethenyl or phenylethynyl.

5. The compound according to claim 1, wherein $R^2$ is hydrogen.

6. The compound of claim 1, wherein the substituents have the following meanings:

$X^3$ is hydrogen, $X^1$ and $X^2$ are Cl, $R^2$ is H and $R^1$ is $CH_3$;
$X^3$ is hydrogen, $X^1$ and $X^2$ are Cl, $R^2$ and $R^1$ are $CH_3$;
$X^3$ is hydrogen, $X^1$ and $X^2$ are Cl, $R^2$ and $R^1$ are H;
$X^3$ is hydrogen, $X^1$ and $X^2$ are Cl, $R^2$ is $CH_3$ and $R^1$ is H; and
$X^3$ is hydrogen, $X^1$ and $X^2$ are F, $R^2$ is H and $R^1$ is $CH_3$.

7. A process for preparing the compound of claim 1, which comprises reacting a compound of formula III

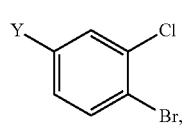

wherein Y is F or Cl,
with a halo-phenol of formula II

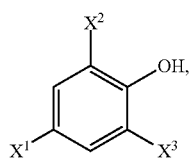

under basic conditions;
reacting the resulting compound of formula IV

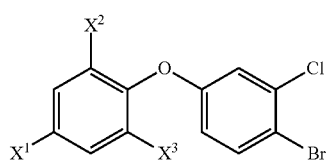

in the presence of a catalyst with isopropylmagnesium bromide followed by a reaction with acetyl chloride;

halogenating the resulting compound of formula V

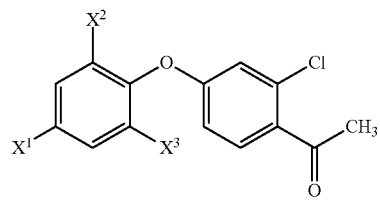

with bromine;
reacting the resulting compound of formula VI

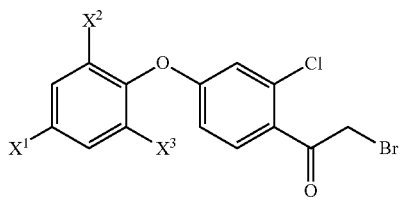

under basic conditions with 1H-1,2,4-triazole;
reacting the resulting compound of formula VII

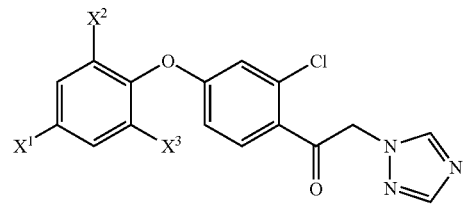

with a compound of formula VIII $R^1$-M,
wherein M is MgBr, MgCl, Li or Na,
and optionally derivatizing the resulting compound of formula I.A

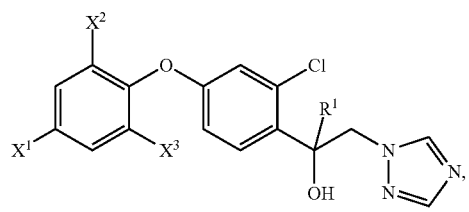

under basic conditions with $R^2$-LG, wherein LG is a nucleophilically replaceable leaving group,
to obtain compounds of formula I.

8. A process for preparing the compound of claim 1, which comprises reacting a compound of formula III

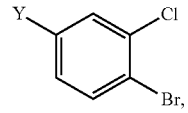   III wherein Y is F or Cl,
in presence of a catalyst with isopropylmagnesium halide followed by a reaction with a compound of formula IX
R¹—COCl,
converting the resulting compound of formula X

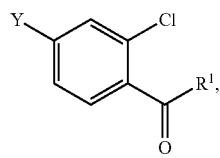   X wherein Y is F or Cl,
under basic conditions with a halo-phenole of formula II

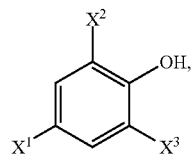   II reacting the resulting compound of formula Va

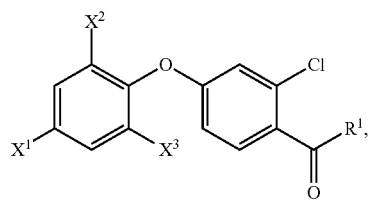   Va with trimethylsulf(ox)onium halide;
reacting the resulting compound of formula XI

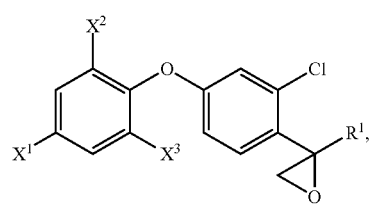   XI under basic conditions with 1H-1,2,4-triazole,
and optionally derivatizing the resulting compound of formula I.A

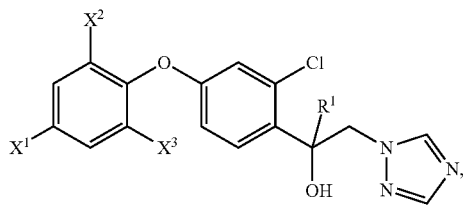   I.A under basic conditions with R²-LG, wherein LG is a nucleophilically replaceable leaving group,
to obtain compounds of formula I.

9. A process for preparing the compound of claim 5, which comprises reacting a compound of formula VII

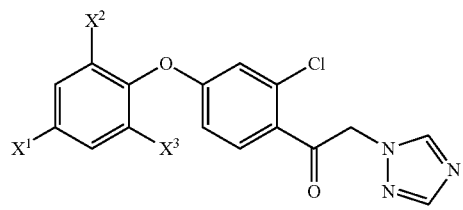   VII with trimethylsulf(ox)onium halide;
and reacting the resulting compound of formula XII

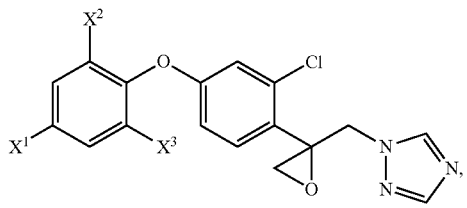   XII with a compound of formula VIII R¹-M,
wherein M is MgBr, MgCl, Li or Na,
and optionally derivatizing the resulting compound of formula I.A

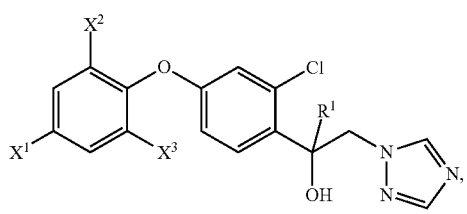   I.A under basic conditions with R²-LG, wherein LG is a nucleophilically replaceable leaving group,
to obtain compounds of formula I.

10. A process for preparing the compound of claim 1, which comprises reacting a compound of formula XI

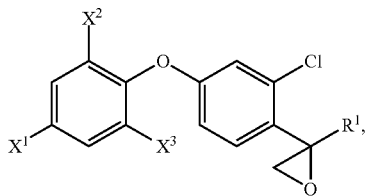

under acidic conditions with $R^2$—OH;
reacting the resulting compound of formula XIII

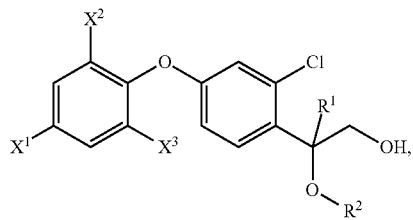

with a halogenating agent or sulfonating agent;
and reacting the resulting compound of formula XIV

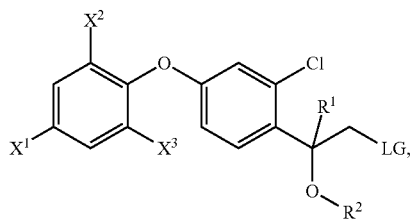

wherein LG is a nucleophilically replaceable leaving group with 1H-1,2,4-triazole, to obtain compounds I.

11. An agrochemical composition comprising an auxiliary and at least one compound of formula I, as defined in claim 1, an N-oxide or an agriculturally acceptable salt thereof.

12. The compositions according to claim 11, comprising additionally a further active substance.

13. A method for combating phytopathogenic fungi comprising contacting the fungi, or their food supply, habitat or breeding grounds with a compound of claim 1.

14. The method of claim 13, wherein $X^1$ and $X^2$ are independently of each other selected from F and Cl.

15. The method of claim 13, wherein $X^3$ is hydrogen, F or Cl.

16. The method of claim 13, wherein $R^1$ is hydrogen, $C_1$-$C_4$-alkyl, allyl, $C_2$-$C_6$-alkynyl, cyclopropyl, cyclopropylmethyl, phenyl, benzyl, phenylethenyl or phenylethynyl.

17. The method of claim 13, wherein $R^2$ is hydrogen.

18. The method of claim 13, wherein the substituents have the following meanings:

$X^3$ is hydrogen, $X^1$ and $X^2$ are Cl, $R^2$ is H and $R^1$ is $CH_3$;

$X^3$ is hydrogen, $X^1$ and $X^2$ are Cl, $R^2$ and $R^1$ are $CH_3$;

$X^3$ is hydrogen, $X^1$ and $X^2$ are Cl, $R^2$ and $R^1$ are H;

$X^3$ is hydrogen, $X^1$ and $X^2$ are Cl, $R^2$ is $CH_3$ and $R^1$ is H; and $X^3$ is hydrogen, $X^1$ and $X^2$ are F, $R^2$ is H and $R^1$ is $CH_3$.

19. Seed coated with at least one compound of formula I as defined in claim 1 in an amount of from 0.1 g to 10 kg per 100 kg of seed.

* * * * *